(12) United States Patent
Williams et al.

(10) Patent No.: US 6,199,986 B1
(45) Date of Patent: Mar. 13, 2001

(54) RAPID, AUTOMATIC MEASUREMENT OF THE EYE'S WAVE ABERRATION

(75) Inventors: David R. Williams, Fairport; William J. Vaughn, Rochester; Benjamin D. Singer, Pittsford; Heidi Hofer; Geun-Young Yoon, both of Rochester, all of NY (US); Pablo Artal, Murcia (ES); Juan Luis Aragòn, Murcia (ES); Pedro Prieto, Murcia (ES); Fernando Vargas, Murcia (ES)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/421,892

(22) Filed: Oct. 21, 1999

(51) Int. Cl.⁷ .................................................... A61B 3/10
(52) U.S. Cl. .................................................. 351/221
(58) Field of Search ................................. 351/205, 211, 351/212, 219, 221, 246, 247; 600/108; 606/7, 10–17, 130; 607/88, 89; 128/898; 356/123

(56) References Cited

U.S. PATENT DOCUMENTS

| 4,523,821 | 6/1985 | Lang et al. . |
| 4,632,528 | 12/1986 | Yoshino et al. . |
| 4,721,379 | 1/1988 | L'Esperance . |

(List continued on next page.)

FOREIGN PATENT DOCUMENTS

| DE 42 22 395 A1 | 1/1994 | (DE) . |
| 5-146409 | 6/1993 | (JP) . |
| 06327634 | 11/1994 | (JP) . |
| WO 87/05205 | 9/1987 | (WO) . |
| WO 92/01417 | 2/1992 | (WO) . |
| WO 95/28989 | 11/1995 | (WO) . |
| WO 98/27863 | 7/1998 | (WO) . |

OTHER PUBLICATIONS

C. Labjuhn, et al., Astigmatismuskorrektur durch Laser-thermokeratoplastik (LTK)—Ein Ansatz für die Korrektur-des hohen Astigmatismus nach Perforierender keratoplastik, *Contactologia 18* D (1996), pp. 175–183.

Cohen, Kenneth L. et al., Assessment of the Power and Height of Radial Aspheres Reported by a Computer–assisted Keratoscope, American Journal of Ophthalmology, vol. 119, No. 6, Nov. 30, 1994, pp. 723–732.

Corbett, Melanie C. et al., The Topography of the Normal Cornea, Eur J Implant Ref Surg, vol. 6, Oct. 1994, pp. 286–297.

Maeder, Anthony J. et al., Accurate 3D corneal surface measurement using an automated mapping approach, Mar. 1995, pp. 328–334.

(List continued on next page.)

*Primary Examiner*—George Manuel
(74) *Attorney, Agent, or Firm*—Blank Rome Comisky & McCauley LLP

(57) ABSTRACT

A wavefront aberration of an eye is determined, e.g., in real time. The eye is illuminated, and the light reflected from the retina is converted into spots with a device such as a Hartmann-Shack detector. The displacement of each spot from where it would be in the absence of aberration allows calculation of the aberration. Each spot is located by an iterative technique in which a corresponding centroid is located in a box drawn on the image data, a smaller box is defined around the centroid, the centroid is located in the smaller box, and so on. The wavefront aberration is calculated from the centroid locations by using a matrix in which unusable data can be eliminated simply by eliminating rows of the matrix. Aberrations for different pupil sizes are handled in data taken for a single pupil size by renormalization.

62 Claims, 11 Drawing Sheets

U.S. PATENT DOCUMENTS

| | | |
|---|---|---|
| 4,764,930 | 8/1988 | Bille et al. . |
| 4,838,679 | 6/1989 | Bille . |
| 4,848,340 | 7/1989 | Bille et al. . |
| 4,881,808 | 11/1989 | Bille et al. . |
| 4,991,953 | 2/1991 | Pflibsen et al. . |
| 5,062,702 | 11/1991 | Bille . |
| 5,114,628 | 5/1992 | Höfer et al. . |
| 5,139,022 | 8/1992 | Lempert . |
| 5,159,361 | 10/1992 | Cambier et al. . |
| 5,177,511 | 1/1993 | Feuerstein et al. . |
| 5,184,157 | 2/1993 | Ichihashi et al. . |
| 5,198,845 | 3/1993 | Triller . |
| 5,202,709 | 4/1993 | Ichihashi et al. . |
| 5,214,456 | 5/1993 | Gersten . |
| 5,229,889 | 7/1993 | Kittell . |
| 5,233,174 | 8/1993 | Zmek . |
| 5,243,367 | 9/1993 | Spellitz et al. . |
| 5,258,791 | 11/1993 | Penny et al. . |
| 5,293,871 | 3/1994 | Reinstein et al. . |
| 5,307,097 | 4/1994 | Baker . |
| 5,404,884 | 4/1995 | Lempert . |
| 5,418,714 | 5/1995 | Sarver . |
| 5,442,412 | 8/1995 | Frey et al. . |
| 5,452,031 | 9/1995 | Ducharme . |
| 5,473,392 | 12/1995 | Klopotek . |
| 5,474,548 | 12/1995 | Knopp et al. . |
| 5,475,452 | 12/1995 | Kuhn et al. . |
| 5,491,524 | 2/1996 | Hellmuth et al. . |
| 5,493,391 | 2/1996 | Neal et al. . |
| 5,502,518 | 3/1996 | Lieberman . |
| 5,512,965 | 4/1996 | Snook . |
| 5,512,966 | 4/1996 | Snook . |
| 5,548,354 | 8/1996 | Kasahara et al. . |
| 5,570,142 | 10/1996 | Lieberman . |
| 5,581,347 | 12/1996 | Le Saux et al. . |
| 5,592,246 | 1/1997 | Kuhn et al. . |
| 5,629,765 | 5/1997 | Schmutz . |
| 5,632,742 | 5/1997 | Frey et al. . |
| 5,722,427 | 3/1998 | Wakil et al. . |
| 5,735,283 | 4/1998 | Snook . |
| 5,740,803 | 4/1998 | Gray et al. . |
| 5,777,719 | 7/1998 | Williams et al. . |
| 5,784,146 | 7/1998 | Nanjo et al. . |
| 5,822,035 | 10/1998 | Bille . |
| 5,841,511 | 11/1998 | D'Souza et al. . |
| 5,847,804 | 12/1998 | Sarver et al. . |
| 5,861,955 | 1/1999 | Gordon . |
| 5,949,521 | 9/1999 | Williams et al. . |
| 6,007,204 * | 12/1999 | Frahrenkrug et al. ............... 351/221 |
| 6,086,204 * | 7/2000 | Magnante ............................. 351/212 |
| 6,095,651 * | 8/2000 | Williams et al. .................... 351/246 |

OTHER PUBLICATIONS

Salmon, Thomas O. & Horner, Douglas G., Comparison of Elevation, Curvature, and Power Descriptors for Corneal Topographic Mapping, 1995, pp. 800–808.

Pavlopoulos, Georgios P. et al., The Effect of Artificial Tears on Computer–assisted Corneal Topography in Normal Eyes and After Penetrating Keratoplasty, Jun. 1995, pp. 712–722.

Roberts, Cynthia, Characterization of the Inherent Error in a Spherically–Biased Corneal Topography System in Mapping a Radially Aspheric Surface, Mar./Apr. 1994, pp. 103–111.

Thornton, Spencer P., Clinical evaluation of corneal topography, 1993, pp. 198–202.

Rabinowitz, Yaron S. et al., Computer–Assisted Corneal Topography in Keratoconus, Nov./Dec. 1989, pp. 400–408.

Wilson, Steven E. et al., Accuracy and Precision of the Corneal Analysis System and the Topographic Modeling System, 1992, pp. 28–35.

Bogan, Stephen, J. et al., Computer–Assisted Videokeratography of Corneal Topography After Radial Keratotomy, Jun. 1991, pp. 834–841.

Bogan, Stephen, J. et al., Classiification of Normal Corneal Topogaphy Based on Computer–Assisted Videokeratography, Jul. 1990, pp. 945–949.

Reidy, James J. et al., The Corneal of Topography of Epikeratophakia, Jan./Feb. 1990, pp. 26–31.

Dingeldein, Steven A. et al., The Topography of Normal Corneas, Apr. 1989, pp. 512–518.

McDonnell, Peter J. et al., Topographic Analysis and Visual Acuity After Radial Keratotomy, Dec. 1983, pp. 692–695.

McDonnell, Peter J. et al., Corneal Topographic Changes after Radial Keratotomy, Jan. 1989, pp. 45–49.

Kiely, P.M. et al., The mean shape of the human cornea, 1982, pp. 1027–1040.

Bafna, S. et al., Corneal Power Calculated by the Paraxial Formula and Snell's Law in Normal Corneas, Feb. 15, 1996, pp. 2589–B434.

Matallana, M. et al., 3–D Video Corneal Topography True Elevation Mapping, Feb. 15, 1996, pp. 2590–B435.

Aoyama, Y. et al., Quantitative evaluation of corneal astigmatism using computed corneal topography and newly developed software, Feb. 15 1996, pp. 2591–B436.

Gelikkol, G. et al., Neural Network Analysis of Videokeratography Following Excimer Laser Photorefractive Keratectomy, Feb. 15, 1996, pp. 2592–B437.

Liang et al., Objective measurement of wave aberrations of the human eye with the use of a Hartmann–Shack wave–front sensor, Journal Optical Society of America, Jul. 1994, vol. 11, No. 7, pp. 1–9.

Walsh et al., Objective technique for the determination of monochromatic aberrations of the human eye, Journal Optical Society of America, Sep. 1984, vol. 1, No. 9, pp. 987–992.

Williams, D. R., Adaptive Optics for High Resolution Retinal Imaging, Investigative Ophthalmology & Visual Science, p. 1055.

Charman, W.N., Wavefront Aberration of the Eye: A Review, Optometry and Vision Science, American Academy of Optometry, vol. 68, No. 8, opp. 574–583.

Bartsch, et al., Resolution Improvement of Confocal Scanning Laser Tomography of Human Fundus, Retinal Imaging Laboratory, Shiley Eye Center–Department of Opthalmology, University of California San Diego, pp. 134–137.

Dreher et al., Active optical depth resolution improvement of laser tomographic scanner, Applied Optics , Feb. 15, 1989, vol. 28, No. 4, pp. 804–808.

Bille et al., Scanning Laser Tomography of the Living Human Eye, Chapter 28, pp. 528–547.

Loew, Murray H., Image Processing, SPIE vol. 2434, pp. 328–334.

* cited by examiner

EFFECT OF LENSLET ARRAY FOCAL LENGTH AND LENSLET DIAMETER

WAVE ABERRRATION STABILITY WITH AND WITHOUT SCANNING

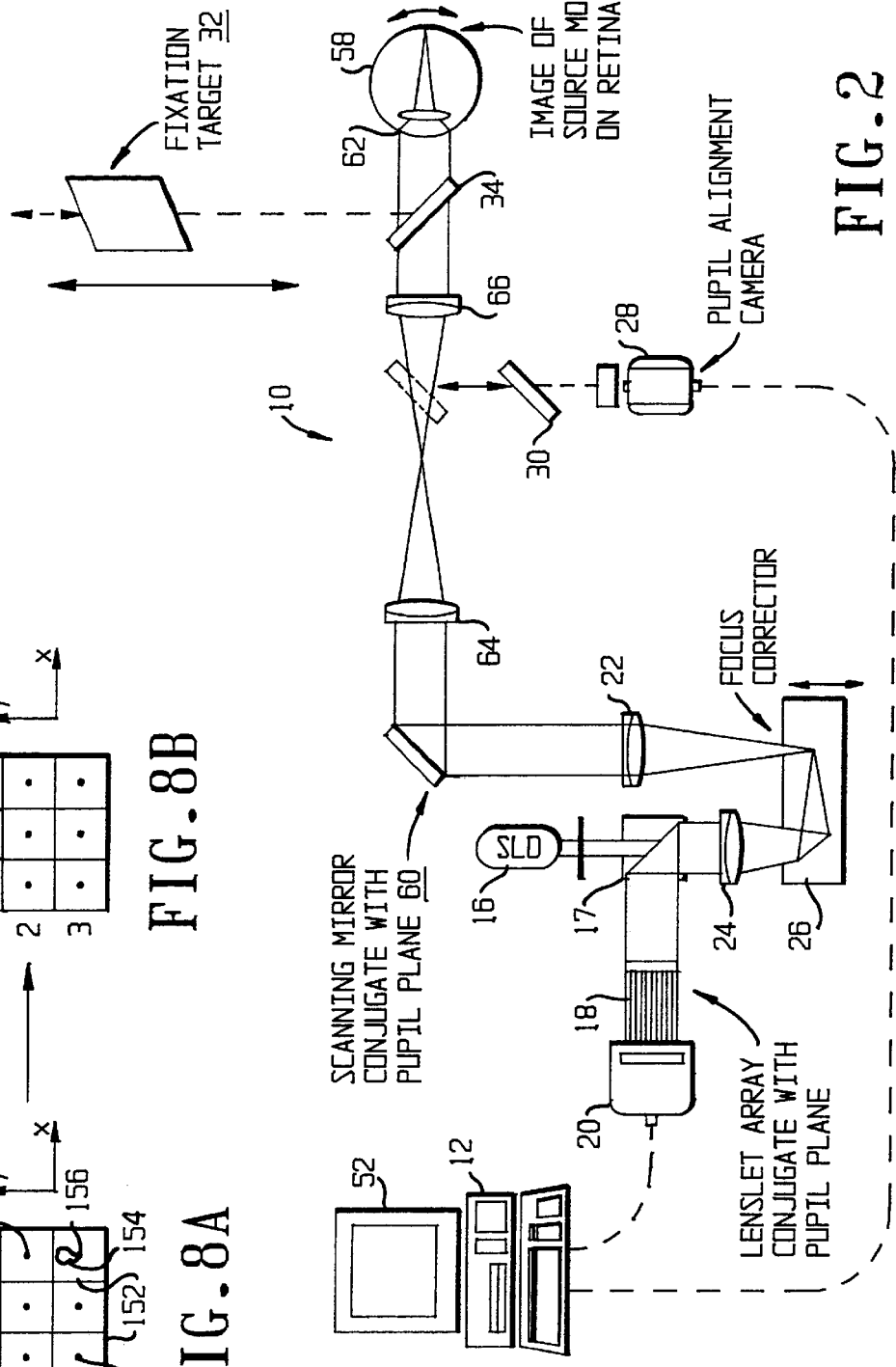
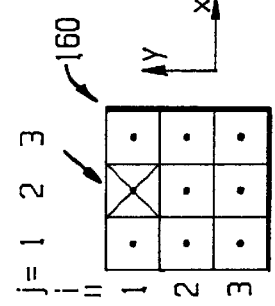
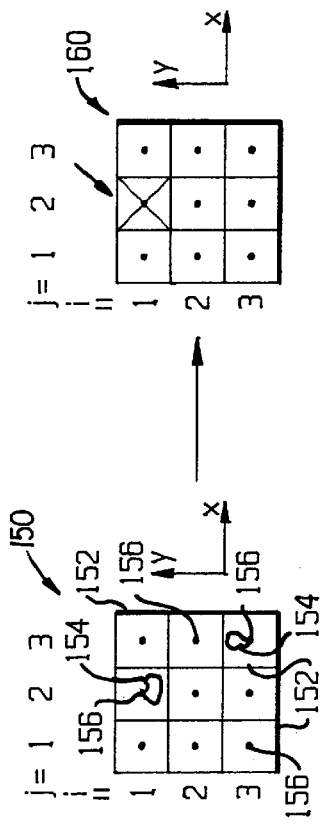
FIG. 8A
FIG. 8B
FIG. 2

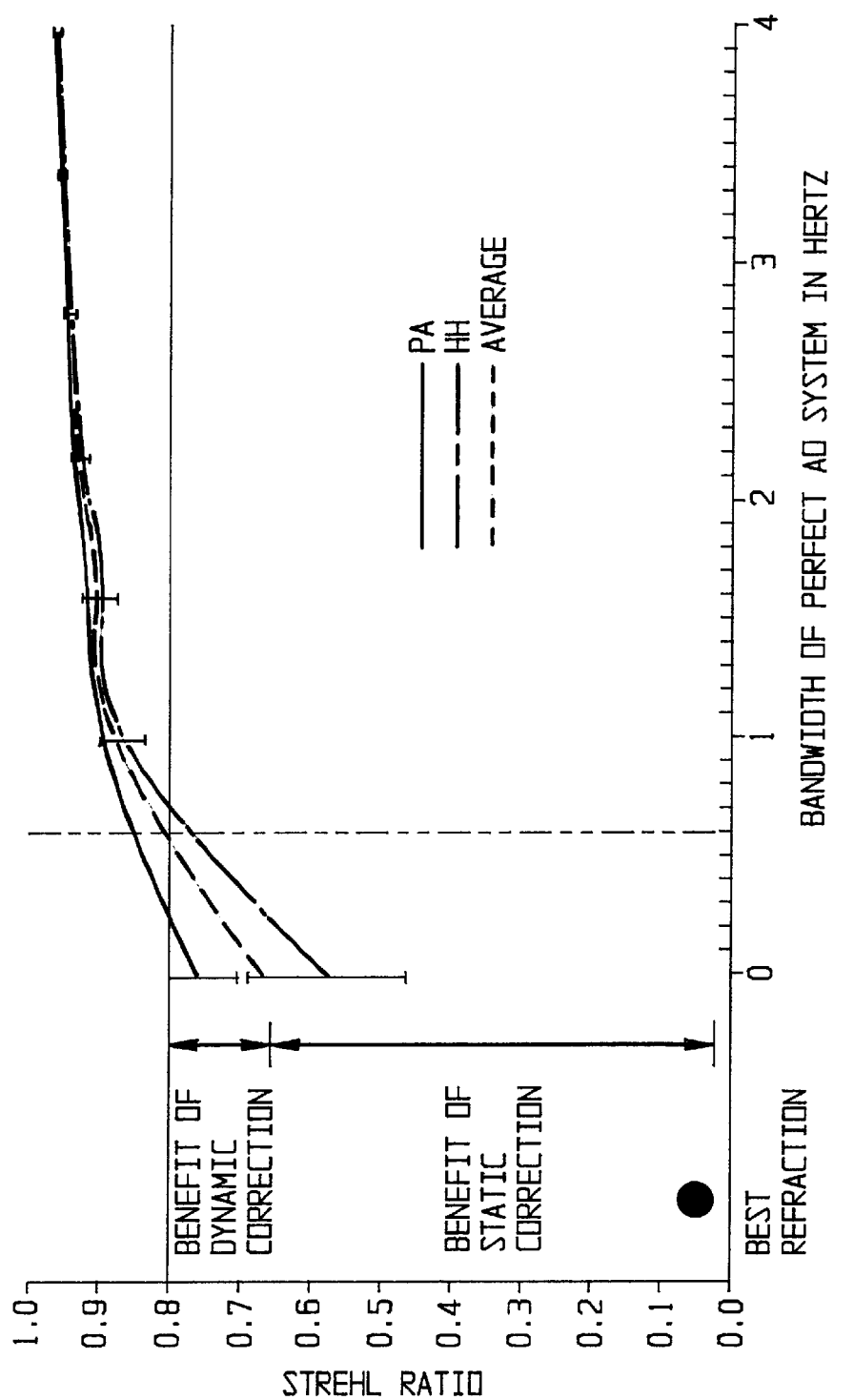
FIG. 18  TIME AVERAGE STREHL RATIO VS. BANDWIDTH OF PERFECT AO SYSTEM TO NATURAL ACCOMMODATION WITH FAR TARGET AND 5.8mm PUPIL

RAPID, AUTOMATIC MEASUREMENT OF THE EYE'S WAVE ABERRATION

BACKGROUND OF THE INVENTION

The present invention is directed to a wavefront sensor and more particularly to a wavefront sensor for ophthalmic applications.

It is known in astronomy to detect wavefront aberrations caused by the atmosphere through the use of a Hartmann-Shack detector. Such detection is disclosed, e.g., in D. M. Alloin and J. M. Mariotti, eds., *Adaptive Optics for Astronomy*, Dordrecht: Kluwer Academic Publishers, 1994. More recently, such a technique has been used to detect wavefront aberrations in the human eye for such purposes as intraocular surgery and contact lens fabrication. Such detection is disclosed, e.g., in Liang et al, "Objective measurement of wave aberrations of the human eye with the user of a Hartmann-Shack wave-front sensor," *Journal of the Optical Society of America*, Vol. 11, No. 7, July, 1994, pp. 1–9, the disclosure of which is hereby incorporated by reference in its entirety into the present disclosure.

That technique will be summarized with reference to FIG. 1. A beam of light from a laser diode or other light source is directed toward the pupil and is incident on the retina. Because the retina is highly absorbing, a beam on the order of four orders of magnitude dimmer than the original beam is reflected by the retina and emerges from the pupil. Typically, the incoming and emergent light follow a common optical path; the incoming light is brought into the common optical path with a beamsplitter.

The emergent beam is applied to a Hartmann-Shack sensor to detect the aberrations. Such a detector includes an array of lenslets that break up the light into an array of spots and focus the spots onto a charge-coupled detector or other two-dimensional light detector. Each spot is located to determine its displacement A from the position which it would occupy in the absence of wavefront aberrations, and the displacements of the spots allow reconstruction of the wavefront and thus detection of the aberrations through known mathematical techniques.

Improvements to the technique of Liang et al are taught in J. Liang and D. R. Williams, "Aberrations and retinal image quality of the normal human eye," *Journal of the Optical Society of America*, Vol. 4, No. 11, November, 1997, pp. 2873–2883 and in U.S. Pat. No. 5,777,719 to Williams et al. The disclosures of that article and of that patent are hereby incorporated by reference in its entirety into the present disclosure. Williams et al teaches techniques for detecting aberrations and for using the aberrations thus detected for eye surgery and the fabrication of intraocular and contact lenses. Moreover, the techniques of those references, unlike that of the Liang et al 1994 article, lend themselves to automation. German published patent application No. DE 42 22 395 A1 teaches a further variation using polarizing optics to control back-scatter from the lenses in the detector setup.

Analysis of the eye presents unique problems and issues not necessarily faced in astronomy. For example, while wavefront sensor systems in astronomy exhibit uniform intensity across their entrance pupil, this is not the case with systems for the eye. The eye, unlike a telescope, is subject to the Stiles-Crawford effect. That effect is a directional sensitivity of the retina, one manifestation of which is an intensity variation across the pupil of the eye when light is reflected from the retina. It exists because illuminated cones radiate more light back toward the center of the pupil than toward the pupil margin. Also, unlike astronomy, stray light from other sources, such as from corneal reflection, can be introduced into the wavefront sensor from the eye, and such stray light can interfere with the measurement of spot placement.

Other problems unique to the eye have been encountered. For example, a subset of the spots that should be formed in the Hartmann-Shack detector cannot be seen, either because the aberrations are unusually large (e.g., a huge aberration caused by a scar or the like can displace or deform the spot so much that the spot's origin cannot be determined or the spot leaves the field of view of the detector altogether), or they are occluded by opacities in the eye's optics or by the pupil. In current wavefront sensors, the loss of any spots frustrates the computation of the wave aberration.

Another problem is that of variable pupil size, as opposed to the fixed pupil of a telescope.

Moreover, there is the issue of real-time operation. Real-time wavefront sensors have been demonstrated in astronomy, but where operation is required at rates typically greater than 300 Hz with closed loop bandwidths greater than 30 Hz. The atmosphere is much too turbulent for real-time compensation at slower rates. On the other hand, present adaptive optics techniques for the eye operate at a very slow rate, less than 0.25 Hz, and do not automatically compute the wave aberration, even with single exposures. Real-time operation is not possible because of the factors described above. Also, these techniques employ relatively long focal length lenslet arrays. Such instruments have high sensitivity to small changes in the slope of the wave aberration at the expense of dynamic range and robustness. Individual spots in the wavefront sensor image often overlap, particularly near the edge of the pupil, making it difficult for automatic centroid spot computation. Such problems can develop especially for a commercial instrument in which operator intervention should be minimized. As a result, these systems cannot measure the wave aberration in a large fraction of human eyes. An optimized wavefront sensor for the eye should therefore properly balance sensitivity and dynamic range, operate in real-time, and be capable of use with a significant fraction of eyes.

The measurement sensitivity of a wavefront sensor for the eye is determined primarily by the focal length of the lenslet array. The smallest measurable wavefront slope is proportional to the focal length. Relatively long focal length (e.g., 97 mm) lenslet arrays used in high sensitivity wavefront sensors for measuring eye wave aberrations typically show a small mean standard deviation of repeated measurements across the pupil of an artificial eye, for example, $\lambda/487$ (at 632.8 nm, the helium-neon laser wavelength) for a 3.4 mm pupil. Moreover, the eye can exhibit a severe wave aberration at the edge of the pupil due to smeared or scarred areas of the eye's tissue. Thus, such wavefront sensors exhibit more sensitivity than necessary and require an algorithm to hunt/locate the migrating spots.

Another challenge to real-time wavefront sensing in the eye is the spatial homogeneity of the spot of light imaged on the retina. Inhomogeneity, caused, for example, by laser speckle or reflectance variations in the underlying retina, disrupts the accuracy of the spot localizatoin. This problem is exacerbated with the short exposures required for real-time operation.

As a result of the above-noted problems with wavefront sensing in the eye, a robust and real-time sensing technique for the eye is not known in the art.

SUMMARY OF THE INVENTION

While many of the above problems have apparently been overcome in astronomy, it will be readily apparent from the foregoing that a need exists in the art for a wavefront sensor capable of handling the unique problems of the eye. It is therefore a primary object of the invention to address such unique problems, which include nonuniform illumination of the pupil due to antenna properties of cones, ocular abnormalities, variable pupil size either among individuals or in the same individual under different levels of illumination, increasing severity of the wave aberration at the edge of the pupil, and spatial inhomogeneity of the retina, which produces centroiding errors.

To achieve the above and other objects, the present invention is directed to a system adapted to overcome such unique problems.

Errors introduced by nonuniform illumination are handled by locating the spots through the following centroiding technique. Once an image is taken, a set of initial boxes is set up on the image. Each initial box is centered around the location where a corresponding spot would be in the absence of wavefront aberration and has a side of length equal to what the inter-spot spacing would be in the absence of wavefront aberration. A first guess of the spot location is produced by finding the intensity centroid of the portion of the image within each initial box. Then a smaller box is drawn, centered on that centroid. The smaller box can be clipped to lie within the initial box. A new centroid is found within that smaller box. That process is iterated until the box size reaches some criterion size, such as a width equal to the full width of half maximum of the diffraction-limited spot. Each step throws away data remote from the centroid found in the previous step, since such data most likely contain noise or systematic errors rather than information useful in locating the spot.

There are two stages used in centroiding the spots. In the first stage, reference boxes are established based on centered reference positions or on the center of the image on the detector (i.e., "from scratch"). The latter technique makes less of an assumption where boxes are located and decides how far out to go as the process runs according to the known size of the lenslet array and number of lenslets. The boxes in the latter technique can form an irregular array, which can be described as being constructed in rings about a center box with the location of the outer boxes being determined in a center-to-outward direction. The size of the boxes using either technique can be adjusted by a parameter entered by the operator or stored in software, for example, 90% of the actual inter-lenslet spacing or 90% of the area of a box having sides equal in length to the inter-lenslet spacing.

Once these boxes are determined, a technique can be used that locates a centroid within an initial box, centers a smaller sized box on that centroid, followed by locating the centroid again, followed by another smaller box centering, and so on until the diffraction limited box size is reached and the final centroid is determined. Alternatively, a technique can be used that starts with an initial box, finds a centroid within that box, centers a smaller decremented box on that centroid, clips as described above, calculates the next centroid, centers a decremented box again, clips again, and so on, all the while maintaining each centroid within the original box. This process also terminates when the diffraction limited box size is reached and the final centroid is determined.

An additional centroid can be calculated on the entire array to locate the center, which is especially used with longer focal length lenslet arrays. Doing so permits compensation for spot migration, which is compensated for by the center of mass of the entire array. Iteratively centroiding is to be contrasted with previous techniques such as simply using thresholding and simply by doing a center of mass of the entire box. The present invention better finds the center and reduces the effects of radiance caused by the dimmer spots of the centroids. The technique according to the present invention also reduces the effects of stray light because those effects are progressively eliminated.

The embodiment just described includes re-centering and removing pixel operations. In another embodiment according to the invention, the boxes can be shrunk first, then translated, and then clipped to a threshold value of intensity, in which only those pixel values above the threshold will be included in the calculation of the centroid. There can also be a variable threshold per box as the box size is reduced to account for data from different pixels.

The centroiding technique using shrinking boxes overcomes a difficulty found in centroiding without shrinking boxes, namely, errors when there are broad intensity gradients such as caused by the Stiles-Crawford effect.

Ocular abnormalities, such as scars, can result in spots deviated far from where they would be in the absence of wavefront aberration. Such spots can come close to, or even overlap, other spots. In fact, such spots can be displaced so far that they disappear from the field of view of the detector altogether. Other ocular abnormalities, such as occlusions, can absorb light, so that no spot is produced at all. To handle such abnormalities, the present invention provides a technique for wavefront reconstruction in the absence of certain data points. Part of the wavefront reconstruction involves manipulation of a matrix whose rows correspond to displacements of the spots from their positions in the absence of aberration. For spots not producing usable data, the rows can simply be deleted from the matrix, or the values contained in such rows can be extrapolated from neighboring rows.

At the heart of this flexibility is the particular data structure, which is a matrix of Zernike mode number in the columns and centroid displacement number in the rows. The matrix is used to calculate the Zernike coefficients to determine the wave aberration of the eye.

Different criteria can be used for determining whether to omit a centroid or not, such as the standard deviation of the light within a box in the center of mass calculation, a position of a point being outside of a box or in a highly unexpected area within the box, or points being occluded totally by corneal defects. Then based on these omitted response or centroids which can be done on a frame by frame basis if desired, one calculates the Zernike modes.

Variable pupil size can be handled either before or after data are taken. If the variable pupil size is to be handled in the same individual, data can be taken twice. If that is not convenient or possible, data can be taken in a larger pupil radius, and then the centroids in a smaller radius can be located. A renormalization procedure is used to provide a matrix to convert the wavefront reconstruction from the larger radius to the smaller one. The variable pupil size results in a variable number of spots used in wavefront reconstruction, which can be handled by varying the number of Zernicke modes used in the reconstruction. The wave aberration is recalculated based on a new radius using software as opposed to changing the actual excluded centroids.

Starting with a valid number of data points, the software can determine a number of Zernike orders, and correspondingly a maximum number of modes that can be accurately calculated. For example, order 0 has mode 1, order 1 has modes 2 and 3, order 2 has modes 4, 5, and 6, etc. Generally, if one calculates particular modes within an order, it is desirable to have all the modes within that order. Therefore, if one were to calculate modes 7 and 8, one would also calculate modes 9 and 10, since all four of those modes are within the third order Zernike equations. A general rule of thumb for calculating the order is (modes+1)(modes+2)/2. Based on this equation, one sees that beginning with the number of available centroids, that number of centroids is divided by two, yielding the maximum calculable modes.

One can determine the highest order that can be accurately calculated based upon the number of lenslets divided by 2, yielding the number of calculable modes. Then, the highest complete number of modes translates to a particular order. For example, 20 centroids yields 10 Zernike modes, which allows one to accurately compute the third order Zernike equations.

The increasing severity of the wavefront aberration at the edge of the pupil can be dealt with as just described.

Spatial inhomogeneity of the retina can be handled through the following techniques. A light source of short coherence length reduces the problem of speckle caused by interference in light of high coherence. In addition, the inhomogeneity can be averaged out by scanning the illuminating light across a short distance of the retina and de-scanning the emergent light.

The above features allow a wavefront sensor according to the present invention to provide fast, robust and accurate centroiding, e.g., up to 50 Hz.

BRIEF DESCRIPTION OF THE DRAWINGS

A better understanding of the present invention can be obtained when the following detailed description of the preferred embodiment is considered in conjunction with the following drawings, in which:

FIG. 2 is a diagram of a wavefront sensor in accordance with a preferred embodiment of the present invention;

FIGS. 8A and 8B illustrate hypothetical arrays used in calculating Zernike coefficients;

FIG. 18 shows time averaged Strehl ratio versus bandwidth of a perfect adaptive optical system for natural accommodation with far target and 5.8 mm pupil.

DETAILED DESCRIPTION

Figure 1:
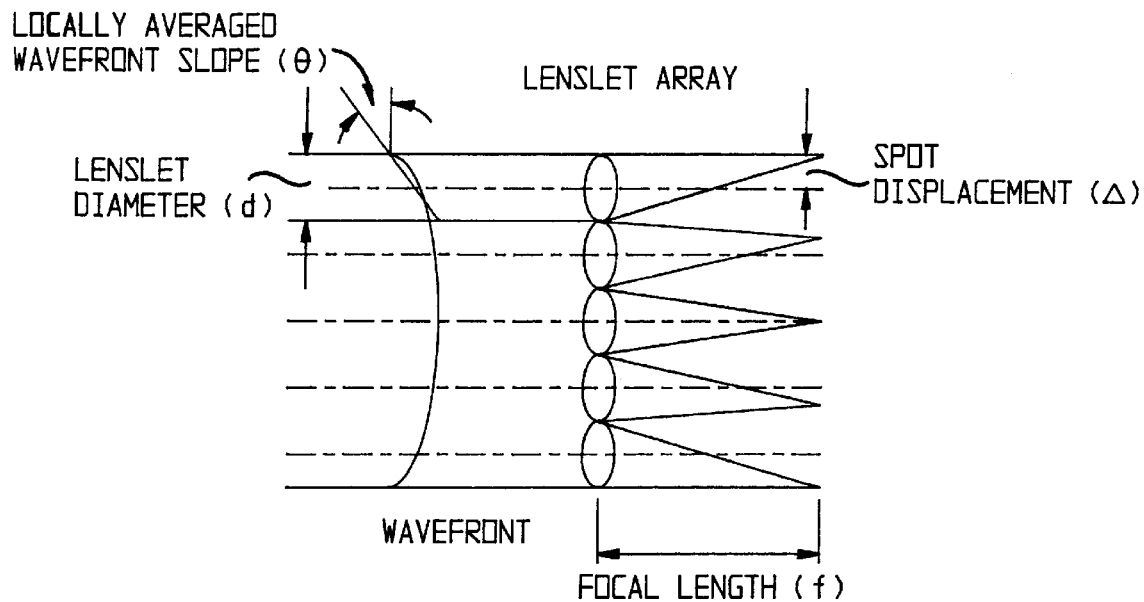
FIG. 1 shows the optics of a Hartmann-Shack detector.

A preferred embodiment and variations thereof will now be set forth in detail with reference to the drawings, in which like reference numerals refer to like components throughout. The detailed description will be organized thus. First, the solutions set forth in the summary will be described in greater detail in turn. Then, the hardware, software and applications of the preferred embodiment will be set forth in that order. Reference will be made throughout to FIG. 2, which shows a wavefront sensor according to the preferred embodiment, and to FIG. 3, which shows a computer for use with the wavefront sensor.

Shrinking Box Centroiding

As is known in the art, the wavefront reconstruction involves determining the displacement of each spot from its ideal location, which is the location that it would occupy in the absence of wavefront aberrations. The spots are located by centroiding, namely, finding the centroid in the image corresponding to each spot. The centroid is an average location weighted by intensity and is analogous to a center of gravity. In other words, the centroid is a mathematical stand-in for the center of the spot. Mathematically, if an area A of the image has an intensity distribution I(x, y), the rectangular coordinates of the centroid within that area are given by:

$$(\bar{x}, \bar{y}) = \left( \frac{\int_A xI(x,y)\,dx\,dy}{\int_A I(x,y)\,dx\,dy}, \frac{\int_A yI(x,y)\,dx\,dy}{\int_A I(x,y)\,dx\,dy} \right)$$

Figure 12:
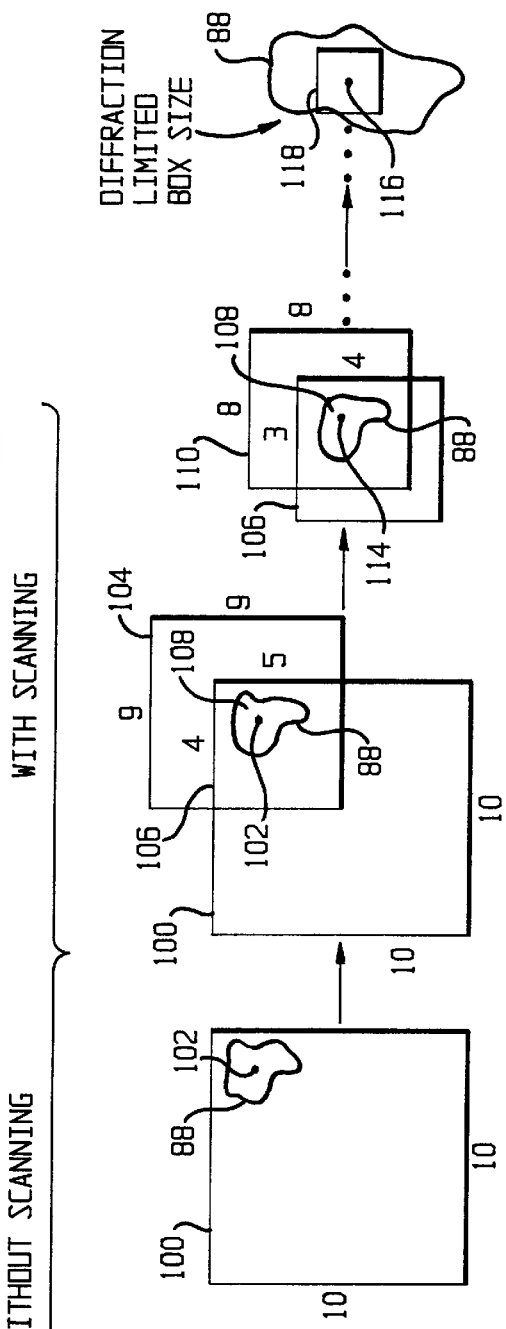

The preferred embodiment uses an iterative centroiding technique to provide robust and accurate centroid location. In one variant, the image is divided into an array of initial boxes, each centered on the ideal location of the spot and having a linear dimension equal to the spacing between the ideal locations of the spots, much like the array shown in FIGS. 8A and 8B. If the quality of the optics of the eye is high enough or the wavefront sensor is made insensitive through use of a short focal length lenslet array, it is likely that each actual image spot from the detector of the camera 20 will fall within a corresponding box of this hypothetical square reference array. FIG. 12 shows such an initial box 100, which in this example measures 10 pixels by 10 pixels.

Figure 10:
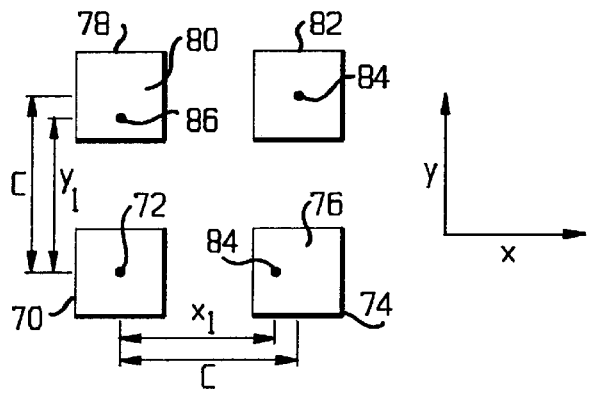
FIGS. 10–12 illustrate a method of centroiding in accordance with an embodiment of the invention.

In another variant shown in FIG. 10, a different process occurs for generating initial boxes. The array of initial boxes generated may or may not wind up being a square array. Instead, it may be an irregular array. In FIG. 10, a first box 70 is identified about a corresponding center point 72. The center point 72 corresponds to an ideal image spot position (i.e., the that a spot would occupy in the absence of wavefront aberrations) at the center of the image of the detector camera 20. From the box 70, all the other reference boxes are generated as follows. With knowledge of the total number of lenslets in the lenslet array, and the magnitude of the lenslet spacing "C", a second box 74 is identified about its own center point 76 spaced one inter-lenslet spacing from the first box 70 along a principal direction (e.g., an "X" direction). The X principal direction corresponds to one of the directions along which the array of ideal center points is defined and corresponds to one of the directions in which the actual lenslets 18 are laid out. In like fashion, another principal direction (e.g., a "Y" direction), orthogonal to the X direction, also corresponds to a direction along which the ideal center points of the lenslet array are located on the detector of the camera 20. Along the Y direction, another box 78, having its center point 80, is identified at the inter-lenslet spacing from the first box 70. Next, in order to identify another box 82 along a diagonal in between the boxes 74 and 78, a centroid is preliminarily calculated for each of the boxes 74 and 78. As shown in FIG. 10, centroids 84 and 86 are found that correspond to these boxes, both of which are located at less than the inter-lenslet spacing from the center point 72 of the box 70 in this example. It is quite possible that these preliminary centroids could be located further removed from the center 72 than the inter-lenslet spacing C, but FIG. 10 is merely illustrative of the technique. Because these centroids are located less than the inter-lenslet spacing from the center 72, a reasonable estimate of where a box 82 should be placed is at a location ($x_1$, $y_1$) that corresponds to the X position of the centroid 84 box 74 and the Y position of the centroid 86 of the box 78. Thus, ($x_1$, $y_1$) is the position determined for a center 84 of the box 82, as shown in FIG. 10. The array is completed by determining successive "rings" (actually squares) of boxes, each of which can be more or less than the inter-lenslet spacing distance from the previous ring. If the spacing in the principal directions, found in the previous ring, is more or less than the inter-lenslet distance, that spacing will be used to find the next set of four boxes in the principal directions for the next ring out from the center. The result is a reference array of boxes that could be irregular or square, and is generated from an initial center box and point with the other reference boxes generated in outer rings, although other methods could be employed. This technique is termed "from scratch."

The actual size of the boxes generated according to either of the techniques just described can be reduced by a factor under control of the operator using the software 13 or programmed into the software 13. For example, the size of a side of any or all the individual boxes may be scaled from the actual inter-lenslet array spacing C or lenslet size (e.g., the box side may only be 90% of the actual inter-lenslet spacing C).

Figure 11:
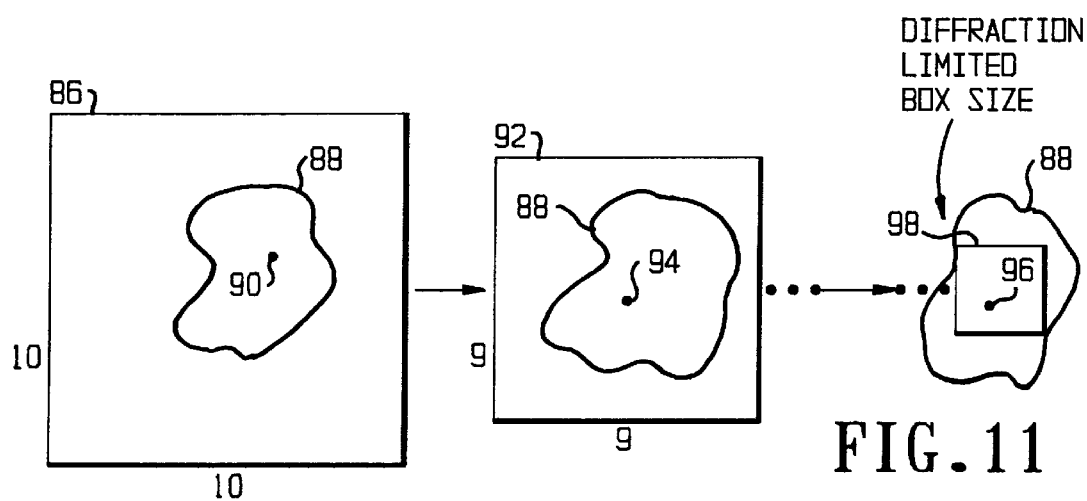

Once the positions of the initial boxes are determined, whether a square array or an irregular array as described above, the process continues to the second stage. Referring now to FIG. 11, a technique is described in which the centroids for all spots corresponding to the image on the detector of the camera 20 are determined in iterative fashion. In FIG. 11, one of the initial boxes (i.e., like one of the boxes in FIGS. 8A and 8B or one of the boxes in FIG. 10) is shown as a box 86 within which an actual spot 88 on the detector of the camera 20 has been located by the software 13. As a first step in the iteration, within the box 86, shown to be of 10×10 pixels in area (although other areas could suffice), a centroid 90 is calculated for the spot 88 in accordance with the equations given above. The centroid 90 likely is not at the actual physical center (not shown) of the box 86. In the next step, the software 13 removes a pixel width and height from a new box 92, which becomes, for example, 9×9 in pixel area, and centers the box 92 about the just calculated centroid 90. The process is repeated within the box 92 with a new centroid 94 being calculated for the spot 88, and then re-centering with a next smaller box centered on the previously calculated centroid and a new centroid calculated for that box and so on. For each progressively smaller box, the centroid is calculated only with respect to image data taken within that box. Once an approximate location of a centroid is determined, it is safe to assume that image data remote from that approximate location represent noise or systematic error such as a ramp from the Stiles-Crawford effect rather than useful information about the location of the spot. Thus, as the boxes become progressively smaller, progressively more noise is excluded. The process terminates when a centroid 96 is calculated for a box (not shown) and the box size is decremented to produce a box 98 that is at or below the diffraction limited box size determined from an optical analysis of the wavefront sensor 10. Once the diffraction limited box size is reached, the previously calculated centroid 96 is the final centroid determined for the spot 88 and the one whose displacement from its ideal reference position is used in calculating the wave aberration for the eye. Some other criterion for terminating iteration might be useful besides reaching diffraction-limited box size.

FIG. 12 illustrates, for the second stage above, an alternative iterative procedure for locating the centroids of the spots on the detector of the camera 20 within the reference boxes. A diffraction limited box size is again used to determine the final centroid for calculating the wave aberration of the eye. In FIG. 12, a box 100 of 10×10 pixel area (although other areas could suffice) is shown that corresponds to one of the reference boxes generated through either of the techniques described above for the first stage. The box 100 is shown to include the spot 88 discussed above. A centroid 102 is calculated for the spot 88 within the box 100 and, as shown in FIG. 12, a new box 104 that is decremented in height and width by 1 pixel (e.g., 9×9 pixels) then is centered on the centroid 102. This particular technique then clips the box 104 to within the box 100, thereby forming a smaller box 106 for the next iteration of centroid location in order to keep the smaller box 106 and thus the new centroid found in the box 106 within the initial reference box 100. The smaller box 106 (e.g., 4×5 pixels) is formed by portions of the sides of the box 100 and portions of the sides of the box 104, as shown in FIG. 12. Within the box 106, a new centroid 108 is calculated, which may or may not be at the same location of the previously calculated centroid 102. Next, a square box 110 of decremented size (e.g., 8×8 pixels) is centered on the new centroid 108, and the process is repeated by clipping the new box 110 to lie within the box 100 (also to lie within the box 106) again to form a new smaller box 112 (e.g., 3×4 pixel area) in which a new centroid 114 is again calculated, which may or may not be at the same location as the centroid 108. The process continues repetitively by centering with another smaller box followed by centroiding, and so on. Finally, a centroid 116 is calculated within a clipped box just prior to reaching the diffraction limited box size and a square box is centered on the centroid 116, which is clipped to a new box 118. If the box 118 is at or smaller than the diffraction limited box size, then the previously calculated centroid 116 is retained and its displacement from its ideal reference on the detector of the camera 20 is used for calculating the wave aberration of the eye. In this manner, the centroids that are calculated in the process are always maintained within the area of the initial box 100. It should be understood that a variety of other centroiding techniques could be used in which boxes are sequentially reduced in size and new centroids are calculated iteratively. These other techniques are included within the scope and spirit of the present invention.

Still another variation can be used. Since two consecutive whole numbers are never both odd or both even, two boxes whose dimensions vary by one pixel in each direction cannot have the same center if they consist of whole pixels. As a consequence, asymmetries can easily appear in the spot tails. To avoid that consequence, the centroiding procedure can be adapted to work with fractional pixels. For example, instead of reducing the box size by shaving off one row of pixels and one column of pixels, the technique using fractional pixels can shave off one-half of a row or column of pixels from each side. The contribution of each fractional pixel to the centroid is considered to be the corresponding fraction of the intensity centered in the fraction of the pixel which is used. This technique has been found to produce results of high accuracy in a computationally efficient manner.

The software has a user interface on which the calculated centroids are displayed to the operator. The operator can drag the centroids with a mouse. When an image is acquired, the software automatically computes the centroids in the image. The centroids have a number associated with them, for example, 1–37. Errors in this computation can occur and the user can direct them manually by dragging valid centroids to appropriate locations. The software will re-compute a centroid based on the local light distribution around the location where the dragged spot was left if such a feature is enabled. If a center centroid is dragged to a new center location, the entire set of centroids will be recomputed based on the new center, if such a feature is enabled.

The centroids can be computed in three ways, any of which can be selected by the user. Under some conditions, these alternatives may reduce the need to manually correct the centroid computation. The first alternative is from scratch, which can be a default. The second option is to use the last computed centroid location as the start estimate for finding the centroids on a new image. The third option uses the stored locations of the reference image that would have been obtained by a perfect eye as the starting point for locating the centroids.

Threshold clipping can occasionally aid in the accuracy of the automated centroid-fitting algorithm. Selecting the threshold, for example, by selecting a "Set Threshold" menu command, brings up a dialogue box, that allows the operator to enter a lower and an upper threshold of image intensities valid for analysis. These values are used for all threshold clipping until another value is entered. A current frame can be threshold clipped and threshold clipping on subsequent frames can be enabled, for example, by using a threshold clip. This feature may be disabled for each search box or for the entire image.

Handling of Missing Data

The wave aberration can be reconstructed when any number of wavefront centroid spots is missing or is of insufficient quality and should be eliminated from the data collected by the camera 20. This could be for a number of reasons, for example, the operator believes the data point is an invalid data point (e.g., two spots in one box). Further, this could be automatically done such that if the data point includes too great a standard deviation from a center, or the data point is too dispersed and the standard deviation of the intensity of the pixels is too great. Further, the centroid may simply be too dim to be recognized, or the standard deviation of the center of mass exceeds the predetermined threshold.

That centroids can be dynamically selected for or excluded from use differs from astronomy applications. The substantially higher light levels available in the ophthalmic applications allow areas of scarring, opacity, or otherwise unreliable data, to easily be excluded from the calculation. Any application of wavefront sensing for the eye, including, for example, autorefraction, design of improved contact or intraocular lenses, refractive surgery or retinal imaging with adaptive optics, will benefit from being able to compute the wave aberration when spots are missing or are of insufficient quality.

Dynamic centroid selection is facilitated using the matrix implementation. The following simplified illustrative example is offered. A hypothetical 3×3 array 150 of reference spots and boxes 152 is shown in FIG. 8A. Each box of the array of reference spots 150 and boxes 152 are designated by an index 1–9 from top to bottom and left to right, although another index ordering scheme could be used. For each reference spot 150 determined by the software 13, there is a centroid 154 displaced in x and y from the corresponding aperture center 156 that also is determined by the software 13 within each box, as will be explained below in more detail. The software 13 determines the x and y displacements of each centroid 154, designated $dx_i$ and $dy_i$, respectively. Thus, the s vector has 18 components, 9 for x and 9 for y, as shown in the matrix equation below. The G matrix is an 18 centroid (or aperture center) by 5 modes matrix (i.e., 18×5) and a is the vector of the Zernike coefficients consisting of the 5 components corresponding to first and second order aberrations (no piston term, as explained below). Thus, s=Ga, or in other words, $$S[18]\ G[18\times 5]\ a[5]$$

$$\begin{bmatrix} dx_1 \\ dx_2 \\ dx_3 \\ dx_4 \\ dx_5 \\ dx_6 \\ \vdots \\ dx_9 \\ dy_1 \\ dy_2 \\ dy_3 \\ dy_4 \\ dy_5 \\ dy_6 \\ \vdots \\ dy_9 \end{bmatrix} = [G] \begin{bmatrix} a_2 \\ a_3 \\ a_4 \\ a_5 \\ a_6 \end{bmatrix}$$

The preferred embodiment allows the elimination of centroid data this using the flexible matrix data structure above. Basically, a portion corresponding to the unreliable data can be eliminated from the matrix, the inverse taken, and new Zernike coefficients calculated. The G matrix is truncated with rows eliminated, depending on the number of Zernike modes to calculate and the number of valid data points one wishes to examine. For every centroid missing or removed by the operator, two rows are removed from the s vector (corresponding to the x and y displacements of that centroid) and the G matrix (corresponding to an aperture center) to form an s' vector and a G' matrix, respectively. An example of the s' vector and the G' matrix is shown below again for a hypothetical 3×3 array 160 of lenslets, but with an index "2" element 166 removed as indicated by the X in FIG. 8B. In other words, for every centroid removed, one $dx_i$ (i=1 to 9) component (e.g., $dx_2$) and one $dy_i$ component (e.g., $dy_2$) are removed to form the 16-element s' vector. The corresponding row integral (aperture center) elements of G simply are removed also to form the 16×5 G' matrix given by:

$$G_{ij}^x = \frac{1}{4b^2} \int_{x_i-b}^{x_i+b} \int_{y_i-b}^{y_i+b} \frac{\partial Z_j}{\partial x} dy\, dx,$$

$$G_{ij}^y = \frac{1}{4b^2} \int_{y_i-b}^{y_i+b} \int_{x_i-b}^{x_i+b} \frac{\partial Z_j}{\partial y} dx\, dy,$$

(rows 2 and 11 of matrix G are removed) with a still having 5 components (i.e., Zernike coefficients 2 to 6). In the above equations, b is one-half the length of the side of a box. Generally, one should include at least twice the number of centroids as the number of Zernike modes to be calculated. Thus, for nine centroids, one would generally wish to calculate four to five Zernike modes.

$$s[16] \quad G'[16 \times 5] \quad a[5]$$

$$\begin{bmatrix} dx_1 \\ dx_3 \\ dx_4 \\ dx_5 \\ dx_6 \\ \vdots \\ dx_9 \\ dy_1 \\ dy_3 \\ dy_4 \\ dy_5 \\ dy_6 \\ \vdots \\ dy_9 \end{bmatrix} = [G'] \begin{bmatrix} a_2 \\ a_3 \\ a_4 \\ a_5 \\ a_6 \end{bmatrix}$$

Figure 9:
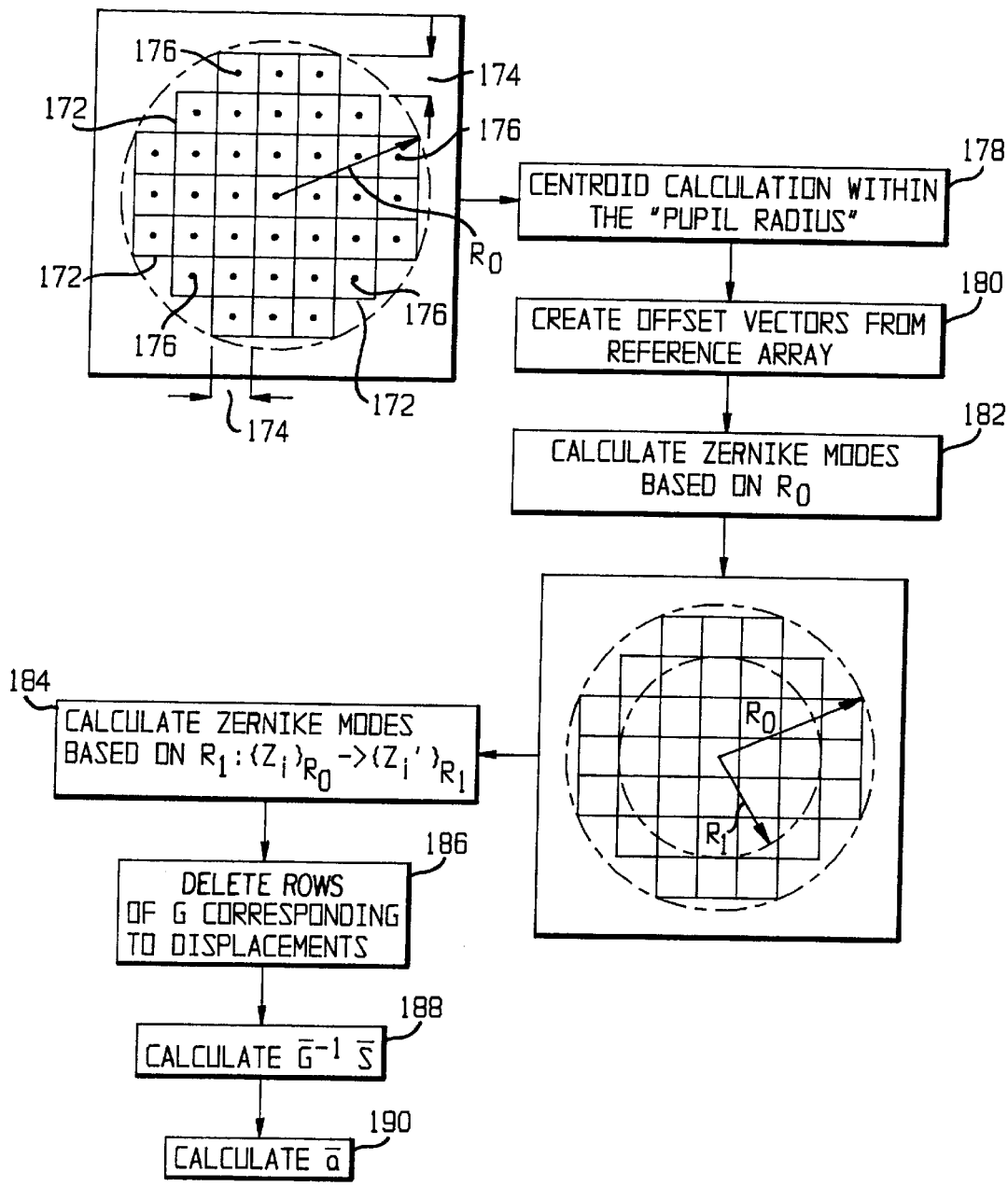
FIG. 9 illustrates a circular region used to capture centroid data within corresponding boxes and a procedure for using the centroid data when the size of the circular area is reduced.

Turning to FIG. 9, if data are to be eliminated, rows are deleted, designated as 186, and once the appropriate G' matrix and s' vector are determined, designated as 188, the a vector must be solved for the corresponding G' and s' as above. The a vector remains the same to determine the wave aberration for the same number of modes as before, but with the displacement data removed.

For a given number of lenslets, the maximum number of Zernike modes that can be used for a reasonably accurate fit is determined. For a given pupil size, which depends on the individual subject being tested, the number of lenslets will be determined. For a given number of lenslets, it has been found that a reasonably accurate wave aberration can be computed with about half this number of Zernike modes. For example, with 37 lenslets, an accurate wave aberration representation can be obtained for approximately fifth order Zernike polynomials consisting of 21 Zernike modes. The above technique will work as long as the number of centroids (lenslets) removed are not too many for the number of Zernike modes to be determined for the a vector. In other words, as the number of lenslets used decreases, it may become necessary to reduce the number of Zernike modes computed in order to follow the above rule of thumb. If too many centroids are eliminated, then the ability to accurately determine the wave aberration for particular Zernike modes is diminished. Another way of stating this is that if too many centroids are eliminated, then the G matrix becomes too "singular" and the SVD will be inaccurate. Following the rule of thumb that twice as many data points should be available as number of Zernike rows calculated, in general, one wishes to use four times the number of rows as columns in the G matrix. Therefore, the results given in the two examples above would be questionable because the number of rows does not exceed the number of columns by a factor of four.

The G' (or G) matrix, which, as discussed above, has elements that are the derivatives of the basis functions averaged over the sub-aperture of each lenslet 18 in the x and y directions, also becomes representative, as a metric, of the number of modes that can be calculated using the SVD technique, in accordance with an embodiment of the invention. The number of entries in the G' matrix provides an indication of the minimum number of displaced centroids (lenslets) required for an accurate calculation of the wave aberration for particular Zernike modes and Zernike order. The preferred embodiment thus not only allows acquisition and analysis of wave aberration data even in subjects who have severely aberrated regions or local occlusions in their pupils, but also provides a metric for accuracy of the calculated wave aberration.

The Zernike coefficients are determined using a data structure matrix, as described above. The rows of the matrix correspond to the Zernike mode number and the columns correspond to the centroid numbers. The matrix multiplied by a vector of the Zernike coefficients is equal to a vector of the displacements of each centroid from its ideal position. The vector of the displacements consists of the displacements in x followed by displacements in y, each subscripted x,y pair of components of the matrix having the same subscript as and corresponding to a particular lenslet. The size of the Zernike coefficient vector is determined by the maximum Zernike mode number. Any of the rows or columns can be eliminated in the calculation depending on the number of centroids and Zernike modes, respectively, required. Once the image data is collected and analyzed, upon elimination of a row or column, the Zernike coefficients can be recomputed on the fly. The software 13 can show where any missing data are located in this matrix. The missing data can be replaced by proxy data consisting of previously taken data or data mimicking another one of the elements of the matrix. Other decision algorithms in the software 13 software can be included to modify the data structure matrix.

Change in Radius of Pupil

The above discussion concerns calculating the wave aberration for centroids within a pupil radius $R_0$ in which the data are acquired. From there, if one wanted to calculate the Zernike modes for a different pupil radius, for example, to account for differences between day and night vision or to exclude large aberrations at the pupil edge, one would preferably do more than simply ignore data from the centroids lying outside the smaller radius. Instead, what is done is to select a new radius, called $R_1$ (see FIG. 9), that captures a lesser number of centroids. The data, however, from the centroids calculated for the radius $R_0$ is not discarded. Instead, it is simply that the Zernike polynomials exterior to $R_1$ are effectively clipped by using a transformation from the Zernike modes for $R_0$ over to the Zernike modes for $R_1$ with renormalization, designated as 184 in FIG. 9. The transformation equation is represented as $\{Z_i\}_{R0} \rightarrow \{Z_i'\}_{R1}$. An explanation of the rationale for its validity, and the means by which it is implemented in accordance with an embodiment of the invention, follows. A set of Zernike coefficients measured over a standard pupil size is renormalized to a set of coefficients measured over a smaller, concentric pupil. As was mentioned above, Zernike polynomials are a set of two variate orthogonal polynomials defined over the unit-circle.

To formulate the procedure used to do so, the wave aberration function is first expressed as:

$$\phi_R(r, \theta) = \sum_{i=2}^{N} b_i Z_i(r, \theta), \quad |r| \leq 1,$$

where $\phi_R$ represents a measured wave aberration of a pupil of radius R (e.g., $R_0$) and $Z_i$ represents the ith Zernike polynomial as a function of polar unit-circle coordinates. The value N is the highest mode that is measured in the wavefront reconstruction. Assume that the b coefficients (which can be expressed as a vector b) are calculated by known methods, but that it is desired that a set of coefficients be determined for the function:

$$\phi_{R'}(rA, \theta) = \sum_{i=2}^{N} b_i Z_i(rA, \theta), \quad |r| \leq 1,$$

which is simply $\phi_R$ evaluated over a smaller, concentric pupil with radius R' (e.g., $R_1$), where A=(R'/R)<1. This function can be thought of as taking a concentric circular "slice" out of the middle of $\phi_R$.

However, the equation just given is not a valid expression for the Zernike representation of $\phi_{R'}$ because such a representation must be expressed in a radial variable that ranges over the whole unit circle. Therefore, the goal is to find the coefficient vector c in the Zernike representation of $\phi_{R'}$, $$\phi_{R'}(r, \theta) = \sum_{i=2}^{N} c_i Z_i(r, \theta), \quad |r| \leq 1,$$

in terms of the vector b and the radius ratio, A. In order to determine the vector c, a standard procedure is used for expressing any function defined over the unit-circle in terms of Zernike modes: integrate the product of the function with each Zernike polynomial over the unit-circle to find the corresponding coefficient. In particular, for $\phi_{R'}$, $$c_i = \frac{1}{\pi} \int_0^{2\pi} \int_0^1 \phi_{R'}(rA, \theta) Z_j(r, \theta) r dr d\theta.$$

The above equations allow one to derive the following:

$$c_i = \sum_{j=2}^{N} b_j \frac{1}{\pi} \int_0^{2\pi} \int_0^1 Z_j(rA, \theta) Z_i(r, \theta) r dr d\theta.$$

The equation just given can be expressed as the matrix equation $$c = T_A b$$

with $T_A$ being a sparse matrix whose entries only depend on A. The entries of $T_A$ can be computed using the symbolic integration tools of Mathematica available from Wolfram Research. Alternatively, they can be computed when the lenslet objects are created in the software in accordance with the new pupil size. The latter technique allows "on the fly" calculation, since the matrices are computed "as you go." The results of this integration shows that each $c_i$ term is a weighted sum of selected $b_j$ terms each of which has both an order with the same parity as and is greater than or equal to the order of the $c_i$ term in question. The weights are polynomials in A whose degree is equal to the order of the corresponding $b_j$ term. The sparseness of the $T_A$ is a result of the fact that the double integral is non-zero only when the azimuthal angle functions of the Zernike polynomials agree. This can happen with only one mode per order and only if the order has the same parity as the order of the original $c_i$ term.

It should be noted that this expression for $c_i$ is also dependent upon the number of modes that are used in the original expression of $\phi_R$. Theoretically, all orders of $\phi_R$ are involved in the expression for c, but the expression that is actually used will only involve those modes of $\phi_R$ that are actually measured. Therefore, this method can produce a wave aberration over a smaller pupil without the need to make additional measurements over that smaller pupil, but it can be no more accurate than the original measurement.

The advantage of the above method is that all of the data are still employed. That is, one maintains the information of the wavefront inherent in the Zernike modes. However, the Zernike modes are for a smaller calculated radius instead of being calculated by just clipping the data, which could lead to less accurate results.

In this software calculation of the smaller radius R', it is necessary that the radius be smaller than the initial radius R. If it were desirable to capture a greater number of points from a larger lenslet array, for example, or to expand the radius past $R_0$, one would return to the beginning and select a larger $R_0$, thereby passing more data from the image captured by the camera 20 or recapturing more data. By expanding $R_0$ to a larger area, perhaps one would capture more lenslets. Of course, the Zernike modes for a smaller radius could again be calculated as described above from the data initially captured for the larger radius.

The number of Zernike modes calculable in general is limited to the number of centroids captured. As a rule of thumb, one prefers to have at least twice as many centroids as the number of Zernike modes calculated.

In the user interface for this feature, the following options are available: a choice of pupil diameter which allows the data analysis to proceed for smaller pupil diameters than a maximum value, for example, 6 mm; a choice of Zernike mode range, which allows a choice to be made for a minimum and a maximum Zernike mode to use in computing the wave aberration. The wave aberration is reconstructed from the selected range of Zernike coefficients and for the selected pupil size. The wave aberration can be displayed, for example, as a contour plot with values of plus or minus 0.15 microns ($\lambda/8$ at helium-neon wavelength). The point spread function can be calculated from the wave aberration and is computed by the software 13 as squared amplitude of the Fourier transform of the generalized pupil function of the displayed wave aberration function.

Inhomogeneity and Laser Speckle

As noted above, spatial inhomogeneity in the retina can cause inaccurate measurements. To overcome that inhomogeneity, and more specifically to average out its effects, a scanning and de-scanning technique is used.

Figure 7:
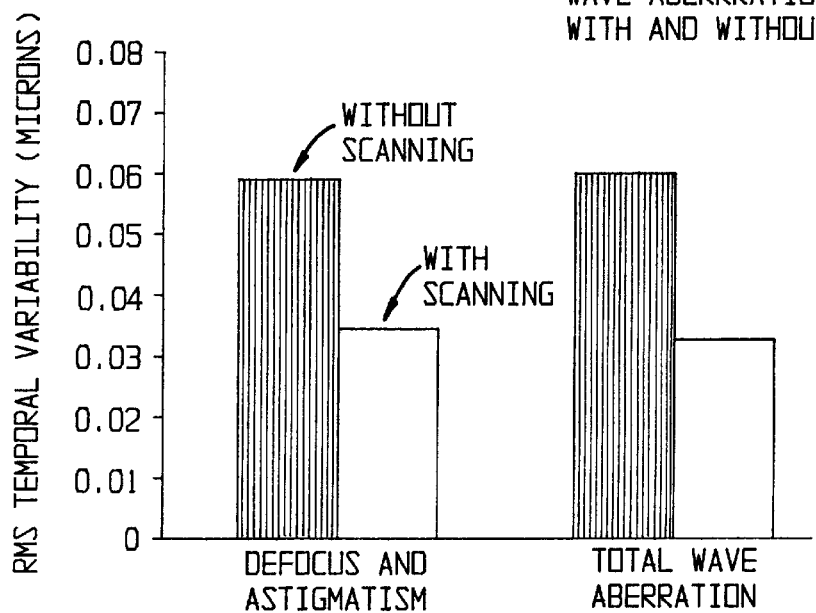
FIG. 7 illustrates the effect of scanning in the wavefront sensor of FIG. 2.
Figure 6:
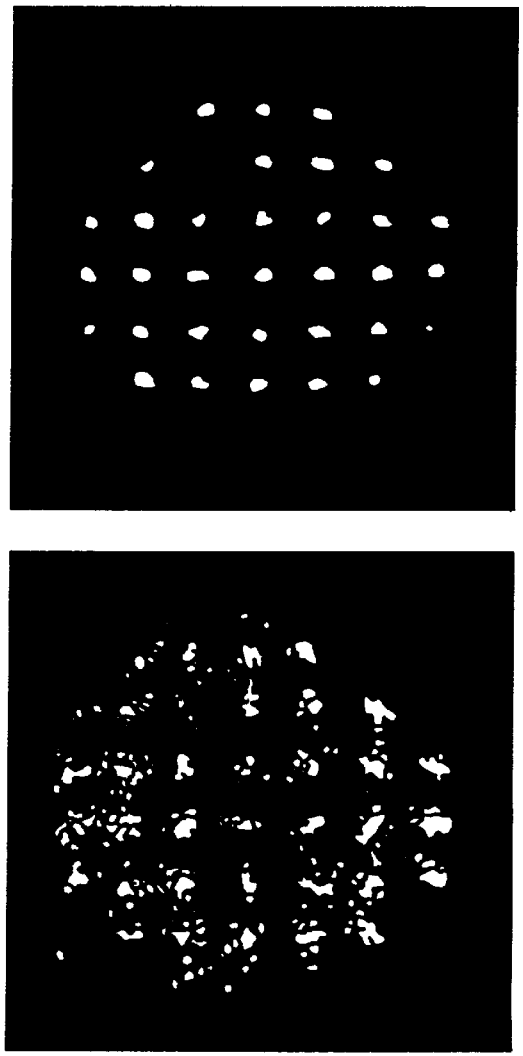
FIG. 6 shows images obtained with and without scanning in the wavefront sensor of FIG. 2.

To implement the scanning and de-scanning, FIG. 2 illustrates a wavefront sensor 10. In order to reduce the problem with short exposures, the wavefront sensor 10 includes a scanning/de-scanning mirror 60 conjugate to the pupil plane 62, and a pair of lenses 64 and 66. The mirror 60 eliminates spatial noise by scanning a point source in a line on the retina, as will be appreciated by those skilled in the art. The angular extent of the scan can be less than 0.5 degrees at a temporal frequency of 400–600 Hz. The angular extent of the scan is kept smaller than the isoplanatic patch size of the eye 58. The temporal frequency is set high enough that there are many scans within a single frame of the detector of the camera 20. By having the light return from the eye 58 through the same scanning optics, it is de-scanned so that there is no movement of the image of the pupil on the lenslet array 18. Thus, spatial noise can be removed without disrupting the wave aberration measurement. FIGS. 6 and 7 compare results obtained with the wavefront sensor 10 with and without scanning/de-scanning.

Scanning is an effective method to remove spatial noise when short exposures of the wavefront sensor 10 are required. This benefit will accrue naturally in a confocal laser ophthalmoscope equipped with adaptive optics. In that case, the same scanning beam that is used for imaging can be used for low noise wavefront sensing. Scanning is not recommended in a commercial instrument designed only to measure the static component of the wave aberration, provided it is possible to either average the results from a number of short exposures, or collect light over a single long exposure. In either case, the recommended total exposure duration is at least 1–2 seconds for eye movements to eliminate spatial noise on their own.

Laser speckle is known in various arts, including holography, and is caused by intereference among various components of a highly coherent light beam. As discussed above, laser speckle degrades the quality of wavefront sensor spots when a coherent laser (usually either a helium-neon or diode laser) is used as the source 16. Conventional laser diodes, when driven above lasing threshold, are coherent sources with spectral half-widths on the order of only a few nanometers. They therefore have very long coherence lengths so that reflections from many surfaces in the eye and in the wavefront sensor 10 can interfere with each other, producing speckle. To reduce speckle, an SLD having a broad spectral half-width (on the order of 20 nm) and a short coherence length of 30 microns can be used. The coherence length of the SLD is nearly independent of the diode's driver current or output power.

The use of longer wavelength, near infrared sources has at least two advantages. First, they are less dazzling for the patient. Second, the maximum permissible exposure is increased so more light can be used while still ensuring patient safety. Infrared light allows the pupil to dilate so that a larger portion of the wave aberration can be measured. Examples of possible light sources for the light source 16 include a 70 nm laser diode by Sharp, a 780 nm SLD by Anritsu, and an 840 nm SLD by Hamamatsu. The 780 nm Anritsu SLD provides clean, tightly focused spots with the least amount of speckle over a wide range of powers and exposure times. The laser diodes perform similarly. The 780 nm SLD is preferable because it typically produces more compact, relatively speckle-free spots in images for a range of different exposure times and powers than the other 840 nm SLD or the 750 nm laser diode. It is also sufficiently far into the infrared to be comfortable for the patient. A larger number of spots are visible with the 780 nm diode than with the 750 nm diode due to the increase in pupil diameter that results from the reduced brightness of the 780 nm diode.

Laser diode spot images always contain a larger amount of speckle than the SLD. It would be difficult to obtain repeatable measurements of the centroid locations using the laser diode, especially at higher powers when the coherence length is longest. When driven under lasing threshold, shorter coherence lengths are possible. However, the output power obtained under threshold may be too low to yield an adequate amount of light reflected from the retina. It may be possible to underrun current laser diodes if long exposure times are used in conjunction with a detector (e.g., CCD) of the camera 20 that integrates throughout the exposure.

Real-Time Wavefront Sensor Hardware

Figure 3:
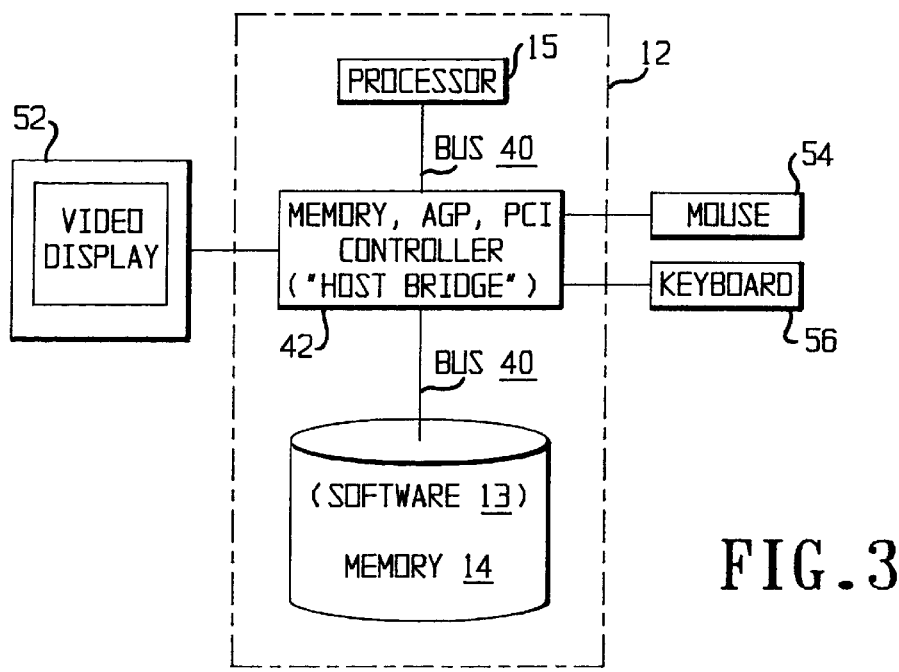
FIG. 3 is a block diagram of a computer of the wavefront sensor of FIG. 2.

A real-time ophthalmic wavefront sensor 10 used to collect and analyze image data from a subject's eye is illustrated in FIG. 2, in accordance with an embodiment of the invention. The wavefront sensor 10 includes a computer 12, for example, a personal computer (PC), and control data acquisition and analysis software 13, as illustrated in FIG. 3. The software 13 can be stored in the PC 12 in memory 14, which can be volatile or non-volatile memory, or a combination of both. The software 13 is executable by processor 15 of the PC 12 to control data acquisition and analysis in the wavefront sensor 10.

The wavefront sensor 10 also includes a light source 16, for example, a gas laser, laser diode, superluminescent diode (SLD), or other source, for providing light exposures during image data collection. The wavefront sensor 10 further includes a beam splitter 17, a lenslet array 18, a camera 20 (e.g., a CCD array detector), a pair of lenses 22 and 24, a focus corrector 26 (e.g., a Porro prism or another single- or double-pass slide mechanism), a scanning/de-scanning mirror 60, another pair of lenses 64 and 66, a pupil-aligning camera 28 and a pupil-aligning reflector 30, and a fixation target 32 and a fixation target reflector 34. A set of four eye pupil-illuminating LEDs (not shown) is included for reflecting light from the subject's eye to aid in aligning the pupil with the wavefront sensor 10.

The PC 12 includes a PCI bus 40 controlled by PCI controller circuitry located within a memory/accelerated graphics port (AGP)/PCI controller 42 ("host bridge"). The host bridge 42 can be a 440LX Integrated Circuit by Intel Corporation, also known as the PCI AGP Controller (PAC). The controller 42 couples the PCI bus 40 to the processor 15 and the memory subsystem 14. The processor 15 can be a Pentium Pro, also by Intel Corporation. A variety of processors could be used for the processor 15 without detracting from the scope and spirit of the invention.

A video display 52, a mouse 54, and a keyboard 56 are also coupled to the host bridge 42, enabling operator interaction with the PC 12.

The wavefront sensor 10 includes additional hardware not shown to simplify the drawings, although their use will be appreciated by those skilled in the art. For example, the wavefront sensor 10 includes hardware for turning the light source 16 and pupil-illuminating LEDs on and off, and hardware for moving the focus corrector 26. For real-time operation, image acquisition is accomplished with a real-time framegrabber, for example, a PCI-bus Bitflow Roadrunner (up to 50 Hz). Also included for real-time operation is a slower PCI Framegrabber for gathering pupil images, for example an Imagenation PXL. The wavefront sensor 10 controls the pupil-illuminating LEDs via either a parallel port of the PC 12 coupled with a custom control circuit, or via a PCI digital 10 card, for example a Keithley MetraByte PIO-24. The focus corrector 26 is controlled either through a serial port of the PC 12 via a serial driver, for example, from Velmex, Inc., or through the same digital IO card used to control the LEDs. A variety of other configurations for the hardware constituting the wavefront sensor 10 are possible, as will be appreciated to those skilled in the art.

The focal length of the lenslet array 18 is reduced relative to that of typical wavefront sensors to optimize performance and help facilitate real-time operation. As illustrated in FIG. 1, by reducing the focal length (e.g., to 40 mm), the spot displacement ($\Delta$) becomes smaller for the same wave aberration, which provides a larger dynamic range for the wavefront sensor 10. The spot diameter also becomes smaller because of the relationship between spot diameter (sd) and focal length given by sd=2.44(f/d)$\lambda$=2.44$\lambda$F# in which d is the lenslet diameter and F# is the F-number of the lenslet, as will be appreciated by those skilled in the art. In FIG. 1, $\theta$ is the locally averaged wavefront slope in front of the lenslet array 18 and is related to the spot displacement and the lenslet focal length by $\theta$=$\Delta$/f, as will also be appreciated by those skilled in the art. The smaller spot diameter gives less error in "centroiding" (i.e., making "centroid" measurements). (A "centroid" is an intensity-weighted balance point of Hartmann-Shack spot image data collected from the detector of the camera 20. Centroiding is a process of locating the spots imaged by the lenslet array 18 on the detector of the camera 20 by calculating the positions of the corresponding centroids in the image data). Increasing lenslet diameter will achieve the same effect just mentioned. Larger lenslets reduce the highest spatial frequency that can be measured in the wave aberration. However, reducing focal length increases dynamic range in the wavefront sensor 10 and decreases the need for operator intervention in measuring the wave aberration. Shorter focal lengths than 24 mm could also be used.

The wavefront sensor 10 should use as short an exposure as possible of the light source 16. This is especially true for a commercial instrument, because it reduces patient discomfort and allows the operator to collect the data with reduced risk of head movement during the exposure. Moreover, a wavefront sensor designed to track the eye's aberrations in real-time, such as would be required in a high resolution fundus camera equipped with adaptive optics, would need to use exposures on the order 30 msec. However, shortening the exposure can reduce accuracy because spatial noise is increased in the spots, which reduces the accuracy of the instrument. This spatial noise can arise from several sources. Reflectance variations can occur across the retina due to, for example, the waveguide properties of cones and absorptance variations in the pigment epithelium. Moreover, when coherent light is used, laser speckle can be produced due to interference, which can exacerbate the non-uniformity of the wavefront sensor spots. These sources of inhomogeneity largely can be removed by using long exposures, on the order of 1–2 seconds. The reason for this is that the eye moves enough on its own during this period to average out the non-uniformities. The light sources described above with respect to laser speckle and long wavelength, particularly the SLD's named, can overcome such problems.

Moreover, laser diode spot images always contain a larger amount of speckle than the SLD. It would be difficult to obtain repeatable measurements of the centroid locations using the laser diode, especially at higher powers when the coherence length is longest. When driven under lasing threshold, a shorter coherence length (i.e., lower coherence) is possible; however, the output power obtained under threshold may be too low to yield an adequate amount of light imaged from the retina. It may be possible to underrun current laser diodes if long exposure times are used in conjunction with a detector of the camera 20 that integrates throughout the exposure, such as a CCD.

The scanning/de-scanning mirror 60, which is conjugate to the pupil plane 62, also eliminates spatial noise, for example, when short exposures of the wavefront sensor 10 are required, by scanning a point source in a line on the retina, as will be appreciated by those skilled in the art. This benefit will accrue naturally in a confocal laser ophthalmoscope equipped with adaptive optics. In that case, the same scanning beam that is used for imaging can be used for low noise wavefront sensing. Scanning is not recommended in a commercial instrument designed only to measure the static component of the wave aberration, provided it is possible to either average the results from a number of short exposures, or collect light over a single long exposure. In either case, the recommended total exposure duration is at least 1–2 seconds for eye movements to help eliminate spatial noise.

The angular extent of the scan of the mirror 60 is kept smaller than the isoplanatic patch size of an eye 58, and can be less than 0.5 degrees at a temporal frequency of 400–600 Hz. The temporal frequency is set high enough that there are many scans within a single frame of the detector of the camera 20. By having the light return from the eye 58 through the same scanning optics, it is de-scanned so that there is no movement of the image of the pupil on the lenslet array 18. Thus, the spatial noise is removed without disrupting measurements made with the wavefront sensor 10.

To initiate data acquisition for determining the wavefront aberration of the eye 58, light from the light source 16 is directed to the eye 58. The light passes through the beam splitter 17, the lens 24, the focus corrector 26, the lens 22 and is reflected off the mirror 60 through the lens 64, the lens 66, the mirror 34, and finally into the eye to be focused onto a spot on the retina that is scanned by the mirror 60. The wavefront sensor 10 images the spot focused on the retina. The image is directed back through the system until it is reflected off the beam splitter 17 and then imaged by the lenslet array 18 onto the detector of the camera 20. The focus corrector 26 is adjusted so that ideally the light entering at the pupil plane 62 of the eye is conjugate with the light entering the lenslet array 18. The spot on the retina effectively becomes a point source for imaging by the array 18.

When an image is acquired by the wavefront sensor 10 from the pupil of the eye 58, whether the wavefront sensor 10 is in real-time mode or in a static mode, the eye 58 must be aligned properly with the wavefront sensor 10. The eye 58 should be optimally centered in two dimensions while the subject is viewing the fixation target 32 during data collection. The pupil camera 28 provides an image of the subject's pupil for alignment purposes. The geometrical center of the pupil or the corneal reflection of the pupil-illuminating LEDs can be used to optimize pupil centering. During image acquisition, the pupil camera 28, which later can be used to confirm subject alignment, acquires a final image of the pupil. The software 13 then turns off all the LEDs on the wavefront sensor 10, turns on the light source 16, and snaps a frame or multiple frames with the wavefront sensor camera 20. The light source 16 is then turned off, which signals the end of image acquisition for the subject. In one embodiment, the view on the computer monitor 52 changes from the pupil image to the image acquired with the camera 20. An entire array of lenslet spots on the detector of the camera 20 should be visible in a displayed Image on the monitor 52. In real-time mode, the wavefront sensor 10 continually acquires, processes, centroids, fits Zernike modes, and reconstructs the wavefront (all at up to 50 Hz) after a key press enters this mode and until another key press ends this mode.

In another scanning wavefront sensor system (not shown), instead of a lenslet array, a single aperture is scanned across the pupil of the eye and the resulting light is imaged onto a single detector. The resulting array of spots is produced temporally rather than spatially, as in the wavefront sensor 10. Nevertheless, with the scanning instrument, centroids would be produced that could be analyzed analogously to the techniques discussed herein, as will be appreciated by those skilled in the art.

The hardware just described operates under the control of software for data acquisition and analysis. The operation of the sensor through that software will now be described.

Data Acquisition and Analysis Software

A more detailed discussion is now presented on the software 13 used for data acquisition and analysis with the wavefront sensors 10. In one embodiment, the software 13 is object-oriented code that provides a user interface, data presentation, and real time aberration acquisition. The software 13 also provides centroiding, variable lenslet number, variable Zernike mode number, missing data, and pupil centering, as will be discussed below in more detail. The software 13 stores the value of the ratio between pupil size of the eye 58 and the pupil size of the wavefront sensor 10, and allows a real-valued scale conversion between the two. The software 13 also can accommodate a variety of lenslet arrays with different lenslet diameters and focal lengths.

Once centroid image data have been collected by the wavefront sensor 10 by execution of the software 13, the wavefront sensor 10 uses the software 13 to calculate the wave aberrations of the eye 58 to a given order and a given number of Zernike polynomial modes, as will be appreciated by those skilled in the art. The highest Zernike mode number for any given Zernike polynomial order is specified by (order+1)(order+2)/2. Using the wavefront sensor 10, it has been found that the maximum number of Zernike modes that can be reconstructed accurately from a least-squares analysis of raw wave aberration data is, very roughly, equal to one-half the number of lenslets in the wavefront sensor 10. To enhance such accuracy, the software 13 has been designed to restrict the number of Zernike modes used.

The software 13 includes a "modal" wavefront reconstruction method to reconstruct the wavefront from the Hartmann-Shack centroid data. The method used by the software 13 to obtain the centroid data from the Hartmann-Shack raw spot data will be described in more detail below. With centroid data available, whether just obtained or previously obtained by the wavefront sensor 10, or loaded from an existing file in the memory 14 or from another memory location, the PC 12 is prepared to calculate the wave aberration of the eye 58. Generally, the wave aberration function is expressed as a linear combination of selected basis functions. The basis functions used here are called Zernike polynomials. The Zernike polynomials are an orthogonal set of two variate polynomials defined over the unit-circle, and allow a simple expression for the residual error in the wavefront after a certain degree of phase compensation is made.

To formulate the procedure used in the software 13 for determining the wave aberration of the eye 58, the wave aberration function, $\phi$, is first expressed as a linear combination of Zernike polynomials, namely, $$\phi(r, \theta) = \sum_{i=2}^{N} a_i Z_i(r, \theta), \quad |r| \leq 1,$$

In that equation, $Z_i$ represents the ith Zernike mode. The summation starts at two since the constant term, called piston, is of no concern and cannot be measured with slope estimates. The highest mode desired to be measured in the wavefront reconstruction is the value N. The maximum value of N in the software 13 is 66, which corresponds to Zernike order ten, although the software 13 could be modified to accommodate higher orders and modes. The actual order used depends upon the number of lenslets 18 within the pupil over which the aberrations are measured. The sub-apertures of the lenslets 18 are typically centered on a square lattice and arranged so that as many as possible fit into the specified pupil. They are numbered from 1 to K from left to right, top to bottom, although another numbering scheme could be used. One example of a lenslet array is a 37-lenslet array in which the lenslets are arranged in seven rows and seven columns, excluding the lenslets that view parts of the image falling outside the pupil. The lenslets in the array form one 3-lenslet row, one 5-lenslet row, three 7-lenslet rows, one 5-lenslet row and one 3-lenslet row and are numbered thus:

|    |    |    | 1  | 2  | 3  |    |    |
|----|----|----|----|----|----|----|----|
|    |    | 4  | 5  | 6  | 7  | 8  |    |
|    | 9  | 10 | 11 | 12 | 13 | 14 | 15 |
|    | 16 | 17 | 18 | 19 | 20 | 21 | 22 |
|    | 23 | 24 | 25 | 26 | 27 | 28 | 29 |
|    |    | 30 | 31 | 32 | 33 | 34 |    |
|    |    |    | 35 | 36 | 37 |    |    |

The wavefront sensor 10 and the software 13 permit selection of a variable "pupil" radius by limiting lenslet points effectively to be within a certain range on the detector of the camera 20. Further, the system permits currently stored data to be normalized to a smaller pupil without discarding data, as will be described below. This is reflected in the flowchart of FIG. 13 also described below. The appropriate wavefront (and ultimately, an ablation pattern) can be calculated, for example, in determining the wave aberration for a 3 mm pupil in normal lighting when the captured data is from a 6 mm pupil in dim lighting. In general, it is desirable to maximize the calculated pupil for imaging applications.

The general procedure by which sub-apertures of the lenslets 18 are determined to be within the pupil radius of the wavefront sensor 10 is as follows. A priori, the size of the "pupil" radius or radius of image that is necessary to capture all the centroids is calculated. This is done based on the inter-lenslet spacing of the lenslets 18 as well as the number of lenslets 18 in the image. An advantage of this is that it eliminates other portions of the captured image from the camera 20 from having to be included in the location and calculation of centroids. As illustrated in FIG. 9, there is a circular area 170 of radius $R_0$, which should capture each centroid within its corresponding box 172 having a side equal to inter-lenslet spacing 174. It is from within this area that centroid calculations are performed, as will be described below. The individual centroids are calculated within that pupil radius, and from the calculated centroids as compared to a reference array of ideal centroids (i.e., centered at positions 176 in FIG. 9), which can either be just a derived reference array or could actually be created using a plane wave input to the wavefront sensor 10 to take into account optical aberrations of the optics. Using offset vectors (i.e., centroid displacements) from that reference array, the Zernike modes are calculated based on that initial pupil radius $R_0$. In FIG. 9, the centroid calculation with the pupil radius is designated as 178, the creation of the offset vectors from the reference array is designated as 180, and the calculation of the Zernike modes based on $R_0$ is designated as 182. Then, centroiding is carried out using any of the techniques described above.

Once the centroids are known, the wave aberration can be calculated using the Zernike coefficients as follows. Referring again to the equation for the wave aberration given above, and taking its derivatives with respect to the x and y yields 2K equations. The 2K derivatives are evaluated over the array of subapertures of the lenslets 18. The equations can be expressed as follows (the functional arguments have been suppressed here):

$$\left.\frac{\partial \phi}{\partial x}\right|_l = \sum_{i=2}^{i=N} a_i \left(\frac{\partial Z_i}{\partial x}\right)_l \quad (l = 1, 2, ..., K),$$

$$\left.\frac{\partial \phi}{\partial y}\right|_l = \sum_{i=2}^{i=N} a_i \left(\frac{\partial Z_i}{\partial y}\right)_l \quad (l = 1, 2, ..., K),$$

where $(\ )_l$ represents taking an average over sub-aperture l. Although calculation of the wave aberration from knowledge of the Zernike coefficients is well-known, a matrix method is used to determine the Zernike coefficients in accordance with an embodiment of the invention. As already noted, the two equations just set forth can be rewritten in matrix form as:

$$s = \begin{bmatrix} s^x \\ s^y \end{bmatrix} = \begin{bmatrix} G^x \\ G^y \end{bmatrix} a = Ga,$$

where $s^x$ and $s^y$ are the vectors of slope estimates obtained from the movement of the centroids of the lenslet spots in the x and y directions on the detector of the camera 20, respectively. In other words, s is simply the displacements dx and dy of the centroids from the positions that they would occupy in the absence of wavefront aberration. Of note, the number of Zernike modes in the G matrix can be reduced simply by eliminating columns of the G matrix. The vector a is the array of unknown Zernike coefficients, and $G^x$ and $G^y$ are matrices of derivatives of the basis functions averaged over the sub-aperture of each lenslet 18, in the x and y directions. This matrix is figured as a constant matrix based on the number of lenslets and the lenslet spacing, and is calculated to have at least the greatest number of Zernike modes one might be interested in determining and at least the greatest number of lenslets (×2) that one might be monitoring. That G matrix can be calculated once based on the physical data. If square sub-apertures (e.g., like the box 172 of FIG. 9) are assumed and if b is one-half the sub-aperture side, then $G^x$ and $G^y$ can be expressed as follows, where j (column) indexes the Zernike mode and i (row) indexes the aperture centers:

$$G_{ij}^x = \frac{1}{4b^2} \int_{x_i-b}^{x_i+b} \int_{y_i-b}^{y_i+b} \frac{\partial Z_j}{\partial x} dy\, dx,$$

$$G_{ij}^y = \frac{1}{4b^2} \int_{y_i-b}^{y_i+b} \int_{x_i-b}^{x_i+b} \frac{\partial Z_j}{\partial y} dx\, dy,$$

These two equations can be simplified by defining the antiderivatives of the Zernike polynomials with respect to the x and y variables as $IZ_i^x(x,y) = \int Z_i(x,y) dx$ and $IZ_i^y(x,y) = \int Z_i(x,y) dy$. The software 13 calls these functions "IntZx" and "IntZy" respectively. The above equations can then be expressed in terms of these functions as follows:

$$G_{ij}^x = \frac{1}{4b^2} [IZ_j^x(x_i+b, y_i+b) +$$
$$IZ_j^y(x_i-b, y_i-b) - IZ_j^y(x_i+b, y_i-b) - IZ_j^y(x_i-b, y_i+b)]$$

$$G_{ij}^y = \frac{1}{4b^2} [IZ_j^x(x_i+b, y_i+b) + IZ_j^x(x_i-b, y_i-b) -$$
$$IZ_j^x(x_i+b, y_i-b) - IZ_j^x(x_i-b, y_i+b)]$$

Note that $G^x$ depends on $IZ_i^y(x,y)$ and vice-versa.

Because the equations set forth until now provide an overdetermined system of equations (N−1<2K), a least-squares solution is sought. A procedure called Singular Value Decomposition (SVD) provides a solution to the equation, which is optimal in this sense. In order to determine the Zernike coefficients, essentially a least-square fit is made to the coefficients using the SVD of the matrix equation involving the measured centroid shifts (explained below) in each sub-aperture and the average of the Zernike polynomial derivatives over each sub-aperture. The G matrix is inverted and further processing occurs to yield other matrices from which a can be determined and thus the wave aberration of the eye 58. Applying SVD to the matrix G, matrices U, V and D are obtained such that $G = UDV^t$. D is a diagonal matrix of N−1 "singular" values whereas U is a column-orthonormal matrix with the same dimensions as G, and V is an N−1×N−1 orthonormal matrix. Since the inverse of an orthogonal matrix is simply its transpose and the inverse of a diagonal matrix is simply the diagonal matrix of its reciprocals, we have $$a = G^{-1}s = (VD^{-1}U^t)s,$$

where $G^{-1}$ is the inverse of the G matrix and the superscripted t represents the transpose of a matrix. It can be shown that the wavefront error in this method is proportional to $Tr(D^{-1})$, i.e., the sum of the diagonal elements of $D^{-1}$.

The software 13 selects the lenslet geometry by asking the operator for a pupil radius (or diameter) over which the eye's wave aberration is to be measured. The pupil radius for the eye may be different from the wavefront sensor, but ideally they are the same. From the pupil radius information and the known center-to-center distance of the lenslets 18 as imaged on the detector of the camera 20, the program pre-computes the matrix G for the largest number of lenslets that can be accommodated for that pupil radius for the Zernike modes up to, for example, order ten. (However, the initial order actually used will depend upon the number of lenslets 18 used). After the initial computation, the operator is allowed to have the computer 12 (i.e., the software 13) disregard the slope estimates from selected lenslets 18 as well as have the software 13 compute estimates for a larger or smaller Zernike order, as will be described in more detail below. The number of modes can be determined for any given Zernike order from the expression (order+1)(order+2)/2. See Dai, Gung-Ming (1995), "Theoretical Studies and Computer Simulations of Post-Detection Atmospheric Turbulence Compensation", Ph.D. thesis, Lund University, Lund Sweden, Mahajan, V. N. (1994), "Zernike Circle Polynomials and Optical Aberrations of Systems with Circular Pupils", Engineering & Laboratory Notes, August 1994, pp. S21–S24, Southwell, W. H. (1980), Journal of the Optical Society of America, Vol. 70, p. 998, Tyson, R. K. (1991), Principles of Adaptive Optics, Academic Press, Inc. New York, N.Y., Wang, J. Y. & Silva, D. E. (1980), "Wave-front Interpretation with Zernike Polynomials", Applied Optics, Vol. 19, No. 9, pp. 1510–1518.

As a means of explaining the matrix equations above, the following simplified example is offered. A hypothetical 3×3 array 150 of reference spots and boxes 152 is shown in FIG. 8A. Each box of the array of reference spots 150 and boxes 152 are designated by an index 1–9 from top to bottom and left to right, although another index ordering scheme could be used. For each reference spot 150 determined by the software 13, there is a centroid 154 displaced in x and y from the corresponding aperture center 156 that also is determined by the software 13 within each box, as will be explained below in more detail. The software 13 determines the x and y displacements of each centroid 154, designated $dx_i$ and $dy_i$, respectively for i=1 to 9. Thus, the s vector has 18 components, 9 for x and 9 for y, as shown in the matrix equation below. The G matrix is an 18 centroid (or aperture center) by 5 modes matrix (i.e., 18×5) and a is the vector of the Zernike coefficients consisting of the 5 components corresponding to first and second order aberrations (no piston term, as explained above). The G matrix has the same form as indicated above with b equal to one-half the size of the side of the boxes.

$$S[18] \quad G[18 \times 5] \quad a[5]$$

$$\begin{bmatrix} dx_1 \\ dx_2 \\ dx_3 \\ dx_4 \\ dx_5 \\ dx_6 \\ \vdots \\ dx_9 \\ dy_1 \\ dy_2 \\ dy_3 \\ dy_4 \\ dy_5 \\ dy_6 \\ \vdots \\ dy_9 \end{bmatrix} = [G] \begin{bmatrix} a_2 \\ a_3 \\ a_4 \\ a_5 \\ a_6 \end{bmatrix}$$

Once the magnitudes of the Zernike coefficients are determined, the wave aberration is found, where the only relevant terms are from the sum:

$$\phi = \sum_{i=2}^{6} a_i \, Z_i(x, y)$$

with the matrix elements of G for 18 (j=1 to 18) rows and 5 (i=2 to 6) columns.

Focusing now on particular modules of the software 13, more details are provided below. These modules relate directly to and implement the techniques and procedures described thus far. A flowchart diagram illustrates in FIG. 13 an overall method for the controlled data acquisition and analysis software 13 discussed above in more detail, in accordance with an embodiment of an invention. Control begins in a Begin Exam Process step 200 and proceeds immediately to a Set Parameters step 202. In the Set Parameters step 202, the Optics object is created and the values of the Pupil Scale variable and the Wavefront2PupilScale variable are set to default values based on the particular configuration of the wavefront sensor 10. The values of other variables, such as a pupil radius variable, an inter-lenslet distance variable, and a lenslet focal length variable are also set based upon default values. As an alternative, the variables set in the Set Parameters step 202 may be determined dynamically or asked for and entered by the operator.

Control then proceeds to a Create Lenslets step 210, which is described in more detail below with respect to FIG. 14. Next, control proceeds to a Set Pupil Radius step 215 in which a local pupil radius variable is reset to a radius value determined in step 210. The value of the local pupil radius variable is employed in subsequent steps and is based on the smallest pupil radius that can fit around a set of lenslet objects created in step 210 that correspond to a set of lenslets within the radius. Control then proceeds to a Get Image step 220 in which an image of the retina is captured by the wavefront sensor 10 for processing. As an alternative, the image can be retrieved from a file stored in the memory 14 of the computing system 12 (FIGS. 2 and 3) or other memory.

Following the Get Image step 220, control proceeds to a Generate Reference Array step 230 in which a reference object is created. The reference object contains a set of points that represent aperture center points (like those of FIGS. 8A and 8B) of each lenslet in the set of lenslets created in step 210. The reference array is employed in a Generate Valid Zernike Modes step 270 described in more detail below. The use of a reference array and the generation of Zernike modes has been described above. Control proceeds to a Locate Centroids step 250 in which a centroid is generated for each lenslet of the lenslet array created in step 210. The Locate Centroids step 250 is described in more detail below with respect to FIG. 15.

Following the Locate Centroids step 250, control proceeds to a Select Centroids step 260 in which the operator may set, adjust, or eliminate individual centroids generated in the Locate Centroid step 250, as discussed above. Control then proceeds to the Generate Valid Zernike Modes step 270 in which Zernike modes are generated based on the lenslets 18, the centroids, and the reference arrays, as described above. Once the Zernike modes are generated, then control proceeds to a Reconstruct Wavefront step 280 in which the wavefront of the image captured in step 220 is reconstructed based on the Zernike modes calculated in step 270. The reconstruction of the wavefront based on the Zernike modes is accomplished once the Zernike coefficients are determined using the matrix approach discussed above according to the invention. Following the Reconstruct Wavefront step 280, control proceeds to a parameter change process A, which is described in detail below in conjunction with FIG. 16, and which relates to the discussion above regarding centroid elimination and pupil radius change.

Referring again to FIG. 13, also included in the flowchart of the Begin Examination Process 200 are entry points B, C and D. Entry points B, C, and D enable the Begin Exam Process 200 to be entered at the Set Parameters step 202, the Select Centroids step 260 or the Generate Valid Zernike Modes step 280, respectively. Entry points B, C, and D are described in more detail below with respect to FIG. 16.

Figures 13, 14:
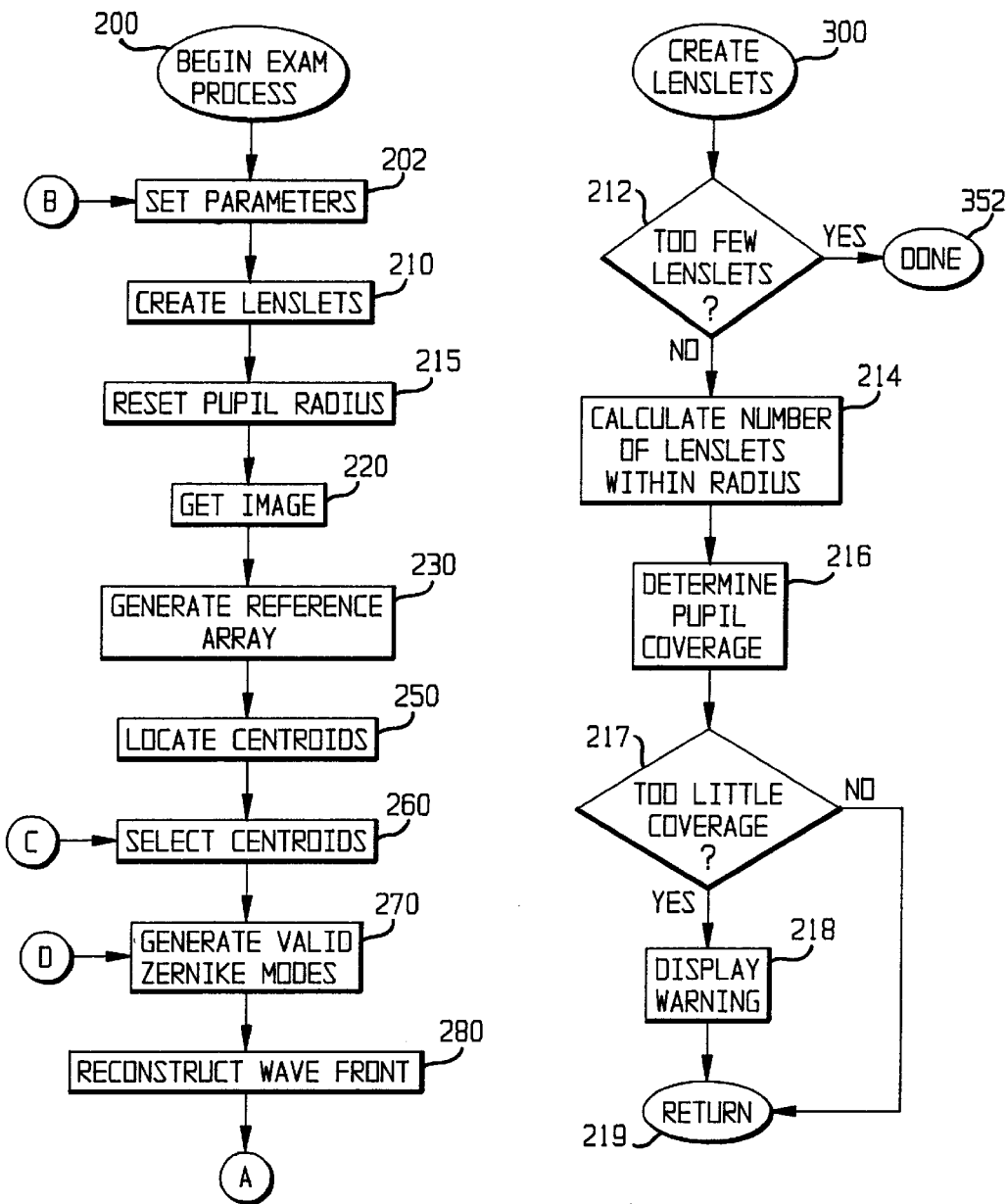
FIG. 13 is a flowchart diagram of a method in accordance with an embodiment of the invention.
FIG. 14 is a flowchart diagram of a module of the method of FIG. 13.

Turning now to FIG. 14, a flowchart is illustrated of a Create Lenslets process 300 corresponding to the Create Lenslets step 210 of the Begin Exam Process 200 (FIG. 13). In the Create Lenslets process 300, control proceeds immediately to a Too Few Lenslets step 212 in which a calculation is performed to determine whether information from operator input will enable a lenslet number parameter greater than a predetermined minimum to be generated for use in determining the wave aberration of the eye 58. If the answers is "No," the process 300 completes in a step 352 and the Begin Examination Process 200 is terminated. As an alternative, a process may be initiated to enable the operator to reselect parameters so that a sufficient number of lenslets are generated. If the answer in step 212 is "Yes," control proceeds to a Calculate Number of Lenslets step 214, which is described in more detail below with respect to FIG. 15. Following the Calculate Number of Lenslets step 214, control proceeds to a Determine Pupil Coverage step 216 in which a ratio between a total area of all the lenslets created (e.g., corresponding to 37 lenslets used as the lenslets 18) in the Create Lenslets step 210 (FIG. 13) and the area of the pupil as determined by the radius set in the Reset Pupil Radius step 215 (FIG. 13) is calculated. Control then proceeds to a Too Little Coverage step 217 in which the ratio calculated in step 214 is compared to both a predetermined minimum value and a predetermined maximum value. For example, the minimum could be 75%. If the ratio is less than or equal to the minimum, indicating that there are too few lenslets (centroids) to accurately reconstruct the wavefront for Zernike modes to a given Zernike order (e.g., as described above), or if the ratio is greater than the maximum, indicating that the Generate Valid Zernike Modes step 270 and the Reconstruct Wavefront step 280 (FIG. 13) are likely to be inaccurate, then control proceeds to a Display Warning step 218. In step 218, an appropriate warning message is displayed on the video screen 52 (FIGS. 2 and 3) to the operator. Control then proceeds to a Return step 219 in which control is returned to the Begin Examination Process 200 and proceeds to the Reset Pupil Radius step 215 (FIG. 13). As an alternative, a process may be initiated to enable the operator to adjust parameters so that the ratio is within appropriate limits. If, in step 217, the ratio is greater than the minimum or less than or equal to the maximum, then control proceeds immediately to the Return step 219, and control proceeds as described above.

Figure 15:
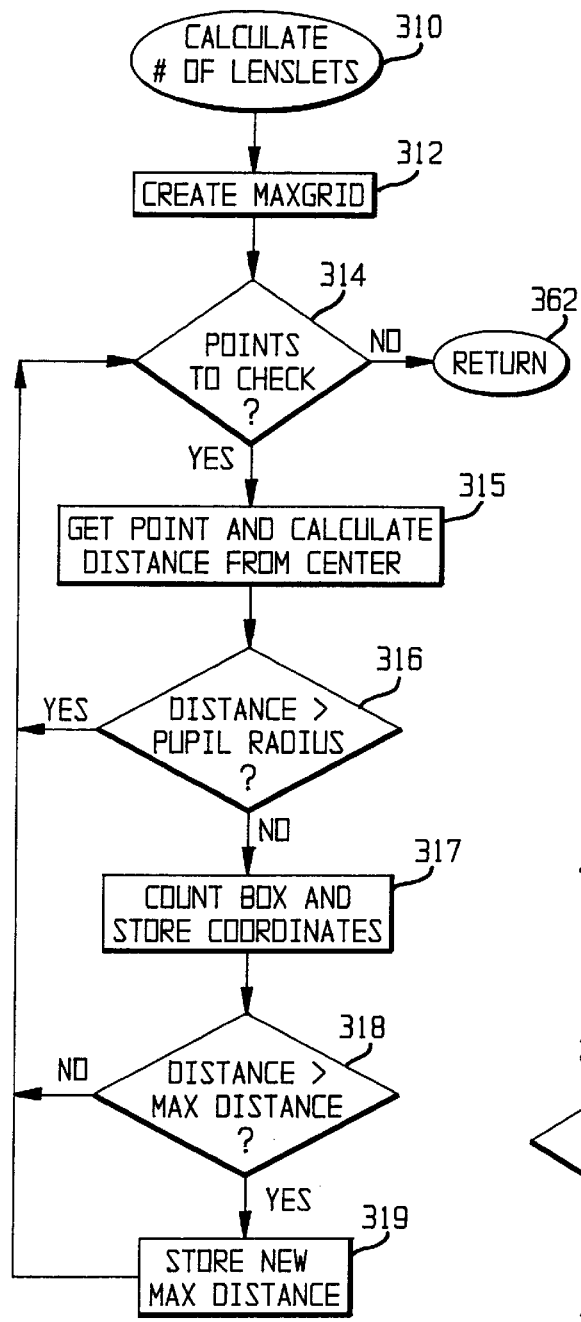
FIG. 15 is another flowchart diagram of a module of the method of FIG. 13.

Turning now to FIG. 15, a flowchart is illustrated of a Calculate Number of Lenslets process 310 corresponding to the Calculate Number of Lenslets step 214 of the Create Lenslets process 300 (FIG. 14). Control proceeds immediately to a Create Maxgrid step 312 in which a matrix of points (grid) is generated corresponding to an array of lenslets with a predetermined maximum number of rows and columns, for example, 19×19. The maximum is a matter of convenience and reserves some memory for the largest lenslet array likely to be encountered. A subset of that memory can be used to create the grid corresponding to the lenslets that are actually used. In addition, a count variable and a max_distance variable are both initialized to the value '0'.

Control then proceeds to a step 314 in which it is determined whether there are points in the Maxgrid array to check. The Maxgrid is used as a maximum boundary within which the locations of boxes and box centers that correspond to the lenslets 18 within the pupil radius are determined in the software 13. The first time through the process 310, the answer is typically "Yes," and control proceeds to a Get Point & Calculate Distance From Center step 315. Process 310 processes points in the grid from left to right and top to bottom, according to design choice. Others directions and sequences are possible. Each point is assumed to be a center of a box with sides equal to the inter-lenslet distance and the distance from the center of the grid to a corner of the box that is farthest from the center of the grid is calculated and retained. If the calculated distance is less than or equal to the pupil radius, indicating that the entire box corresponding to a lenslet is within the pupil, then the count variable is incremented by '1' and the coordinates of that box's center are stored in a first available spot in the Maxgrid array. Control proceeds to a Distance>Max_distance step 318 in which the process 310 determines whether the calculated distance is greater than the previously stored value of the max_distance variable. If the value of the calculated distance is greater than the previously stored value of the max_distance variable, control proceeds to a Store New Max Distance step 319 in which the calculated distance is stored in the max_distance variable, over-writing the previously stored value.

Control then proceeds to Points To Check step 314 when the new value of the max_distance variable is stored in step 319, when it is determined that the calculated distance is less than or equal to the previously stored value in step 318, or when the calculated distance is greater than the pupil radius in step 316, indicating that the box does not fit entirely within the pupil radius. In step 314, the process 310 determines whether there is another point in the Maxgrid array to process and, if so, loops through steps 315, 316, 317, 318 and 319, as described above. Each grid point in the 19×19 array is processed in turn to determine whether it is to be included in the final centroid array.

Referring again to step 314, if the process 310 determines that there are no more points to check, then control proceeds to step 362 in which control is returned to process 300. When control is returned to process 300, the count variable contains the value of the number of boxes, or lenslets, which fit within the pupil radius and the max_distance variable contains the value of distance of the farthest corner of all the boxes that fit within the pupil radius. In addition, the Maxgrid array contains coordinates for each box, or lenslet, which fits within the pupil radius.

Figure 16:
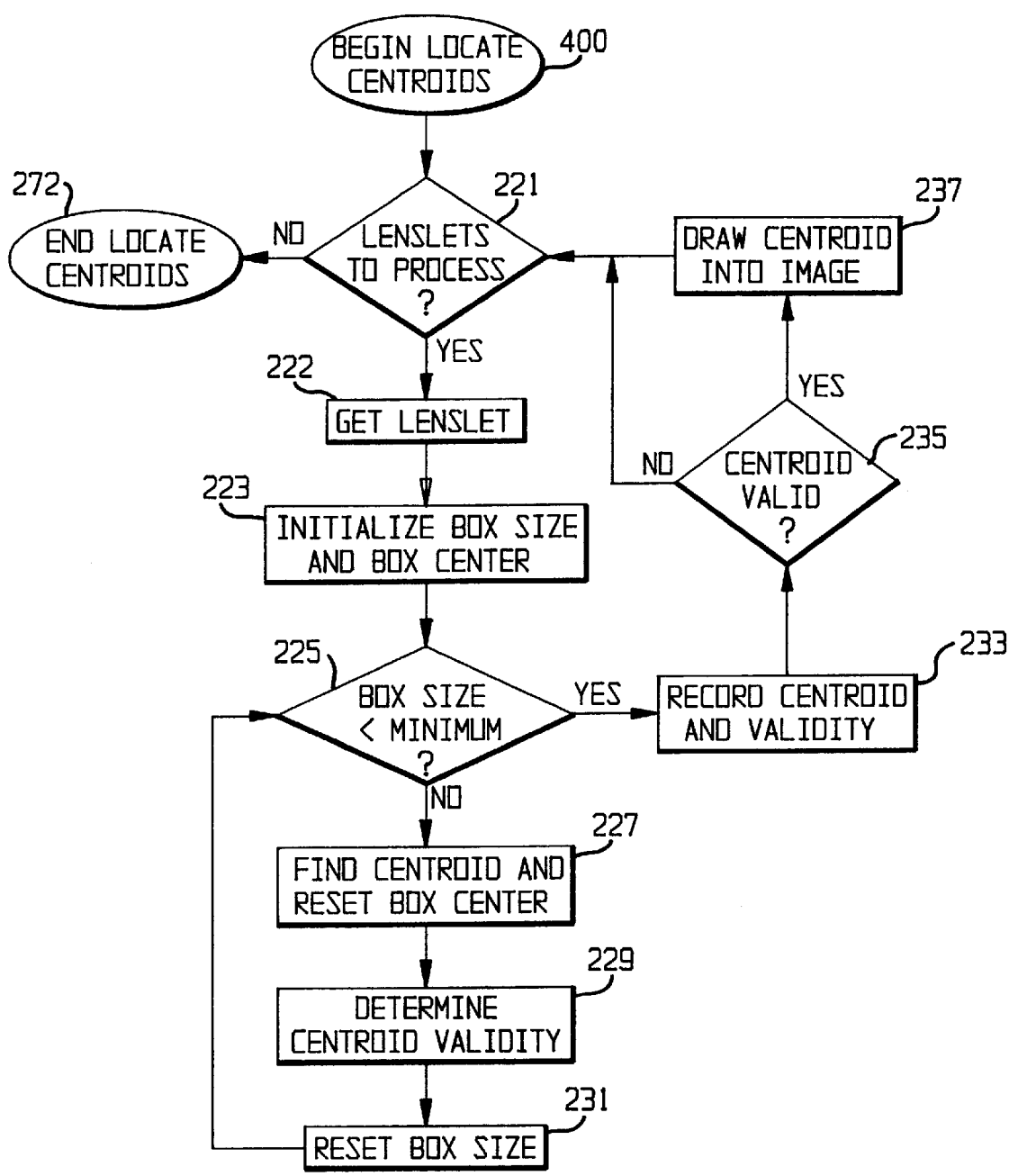
FIG. 16 is another flowchart diagram of a module of the method of FIG. 13.

Turning now to FIG. 16, a flowchart is illustrated of a Locate Centroids Process 400 that corresponds to the Locate Centroids step 250 of the Begin Examination Process 200 (FIG. 13). The Locate Centroids Process 400 determines the location of the centroids as described above using the method of FIGS. 10–12. Control proceeds immediately to a Lenslet To Process step 221 in which the process 400 determines whether there is a lenslet to process that corresponds to the lenslets created in the Create Lenslet step 210 of the Begin Exam Process 200. The first time through, the answer is typically "yes" and control proceeds to a Get Lenslet step 222. The Locate Centroids process 400 starts with the top left lenslet in the lenslet array and processes the array from left to right and top to bottom, according to design. Other directions and sequences are possible.

After a lenslet is selected in step 222, the process 400 proceeds to an Initialize Boxsize & Box Center step 223. In step 223, a "search box" is defined in the image retrieved in step 220 of the process 200 using the coordinates of the center of the selected lenslet as the center of the search box and with the length of the sides equal to the inter-lenslet distance defined in step 202 of process 200. The search box corresponds to the boxes shown in FIGS. 10–12. The centroid for each spot within the search box is calculated as described above. Control then proceeds to a Box Size<Minimum step 225 in which process 400 determines whether the search box is smaller than or equal to a predefined minimum value. The minimum value may be, for example, the size of the diffraction limited spot corresponding to an idealized reference plane wave impinging on and focused by the same lenslet, as will be appreciated by those skilled in the art. If the search box is greater than the predefined minimum value, control proceeds to a Find Centroid & Reset Box Center step 227.

The centroid of the search box corresponds to the center of mass of that search box. In other words, the process 400 weights each pixel in the search box by the intensity of that pixel and defines the centroid. Other parameters may also be used instead of, or in addition to, the average intensity to determine the centroid location. For example, minimum and maximum pixel intensity threshold values may be defined with only pixel values within the thresholds used to calculate the centroid. In step 227, once the centroid of the search box is determined the center of the search box is reset to the coordinates of the centroid and control proceeds to a Determine Centroid Validity step 229. In the disclosed embodiment, in step 260 of the process 200, the operator determines centroid validity. The most common reason for the operator to move a centroid manually is that the centroid location does not appear to be centered on the captured spot of light that is to be centroided. But, in an alternative embodiment, centroid validity may be determined automatically in step 229. For example, a centroid that is outside the borders of the initial search box defined in step 223 may be considered invalid.

After step 229, an iterative centroiding process as described above is performed. That is, control proceeds to a Reset Box Size step 231 in which both the length and width of the search box are reduced by one (or more) pixel. Control then returns to step 225 in which the process 400 determines whether the new box size is less than or equal to the minimum box size again. As described above, a variety of iterative centroid locating processes could be used. Preferably, the optics of the wavefront sensor 10 are of sufficient quality to guarantee that the centroids will be located somewhere within each search box for each iteration. If the search box size is still greater than the minimum value, control proceeds to step 227 as explained above. If the search box size is less than the minimum, then control proceeds to step 223 in which the location of the centroid is stored in the centroid array and the validity of the centroid is stored in a corresponding location in a validity array.

Control then proceeds to a Centroid Valid step 235 in which the appropriate entry in the centroid validity array is checked. If the centroid is valid, then control proceeds to step 237 in which the centroid is drawn in a centroid image or displayed on the display 52 and stored (e.g., in the memory 14). Control then proceeds to step 221 in which the process 400 determines whether there are additional lenslets to process as explained above. If, in step 235, the centroid is determined to be invalid, control proceeds immediately to step 221. Finally, in step 221, if the process 400 determines that there are no more centroids to process, control returns through End Locate Centroids step 272 to step 250 of the process 200 of FIG. 13. With valid centroids and Zernike modes, the wave aberration is determined as described above.

After the wave aberration has been determined, the operator, in one embodiment, can either re-profile the software 13 from the program beginning (FIG. 13, step 200), change program inputs, acquire and analyze data again, while in another embodiment, program inputs can be changed on the fly without reinitialization of other parameters, meaning that a new matrix is computed.

The validity of the Zernike modes can be assessed and the pupil radius can be changed after an initial wave aberration construction or reconstruction, as described above. Such changes vary program flow in the software 13 in reconstructing the wave aberration. For example, the pupil of the eye 58 may initially be dilated for image capture and wave aberration construction and then the operator decides that the wave aberration should be reconstructed over only a central portion at smaller pupil radius. In other words, the radius merely is truncated and all the valid data collected previously can be used again. However, if the pupil radius is increased, then new information is needed that was not gathered previously. A new number of lenslets in the lenslet array 18 may be needed to cover the larger pupil radius as well as a corresponding new number of centroids and reference points used for wave aberration reconstruction.

Whether to change radius can be included for automatic execution in the software 13 in certain embodiments, depending on conditions of the measurements and the desired result. In other embodiments, the operator decides at decision points or the operator decides to reexecute the software 13 from the beginning. In reducing pupil radius, the operator may or may not want to use the same Zernike polynomial order or number of Zernike modes. The operator may want to lower one or both of these. If the same order and modes are desired, the wave aberration is merely re-normalized to the reduced radius size using a new set of Zernike coefficients.

Figure 17:
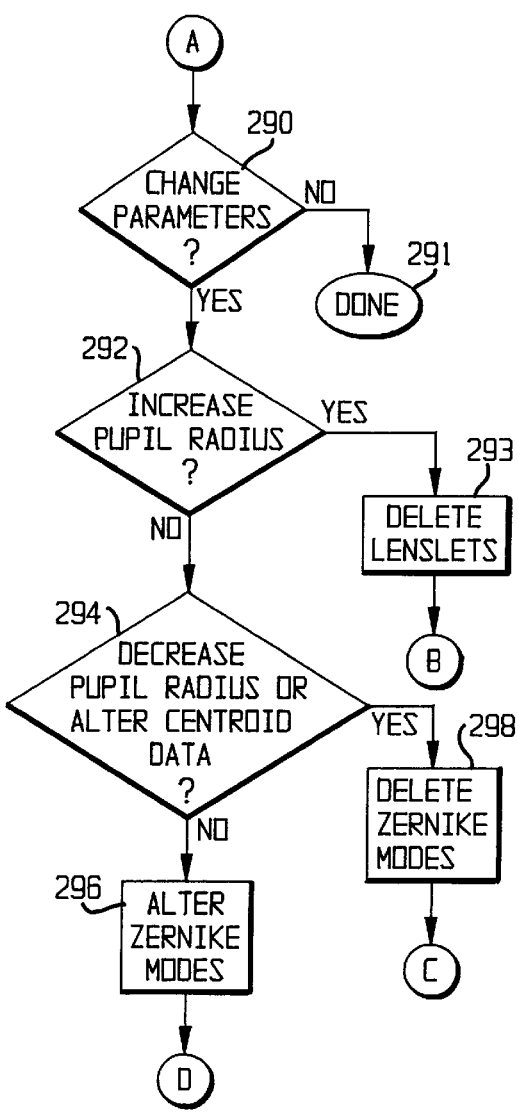
FIG. 17 is another flowchart diagram of a module of the method of FIG. 13.

Turning now to FIG. 17, a flowchart is illustrated of the parameter change process A first introduced above in conjunction with FIG. 13 that allows parameters of the wavefront sensor 10 and data acquisition and analysis to be changed, as discussed above. Control proceeds immediately to a Change Parameters step 290. If the operator does not want to change parameters, the process A and the Begin Examination Process 220 (FIG. 13) are completed in a Done step 291. If the operator chooses to modify parameters in step 290, then control proceeds to step 292 in which it is determined whether one desired modification is an increase in the pupil radius, a modification in the inter-lenslet distance, or a modification in the lenslet focal length. Other modifications can be made in certain embodiments, as will be apparent to those skilled in the art. In that case, control proceeds to step 292 in which the lenslet object created in step 210, the reference object created in step 230, and the Zernike modes created in step 270 can be destroyed to free up memory. Control then proceeds to the B entry point of the Begin Examination Process 200 or the Set Parameters step 202. It should be understood that if any of the conditions that initiate this control sequence are true, then other parameters, such as the number of Zernike modes, may also be modified without changing the sequence.

Referring again to step 292, if the answer is "No," then control proceeds to step 294 in which it is determined whether the desired modification is a decrease in the pupil radius or a modification of the centroid data. If the answer is "Yes," then control proceeds to a Delete Zernike step 298 in which the Zernike modes created in step 270 are destroyed. Control then proceeds to the C entry point of the Begin Examination process 200 or the Select Centroids step 260. If the conditions that initiate this control sequence are true, then the number of Zernike modes also may be changed without changing the sequence.

Referring again to step 294, if the answer is "No," then control proceeds to an Alter Zernike Modes step 296 in which the number of valid Zernike modes is altered, and then proceeds to the D entry point of the Begin Examination Process 200 or the Generate Valid Zernike Modes step 280. At this point, the description of FIG. 13 is complete for the software 13.

Applications and Experimental Data

The present invention has applications in such areas as retinal imaging, fabrication of lenses such as contact lenses and intraocular lenses, and laser refractive surgery. To show the utility of the present invention, some experimental results will be set forth.

One useful application of the real-time wavefront sensor is to measure the stability of the wave aberration of the eye. This is important because the effectiveness of a custom contact lens used to correct higher order aberrations depends on the stability of the eye's wave aberration. If the wave aberration changes either over time or due to changes in viewing conditions, these changes will limit the ability of any static optical element to provide sharp vision. Experiments were performed that address this question and the results are provided in the following sections.

Figure 4:
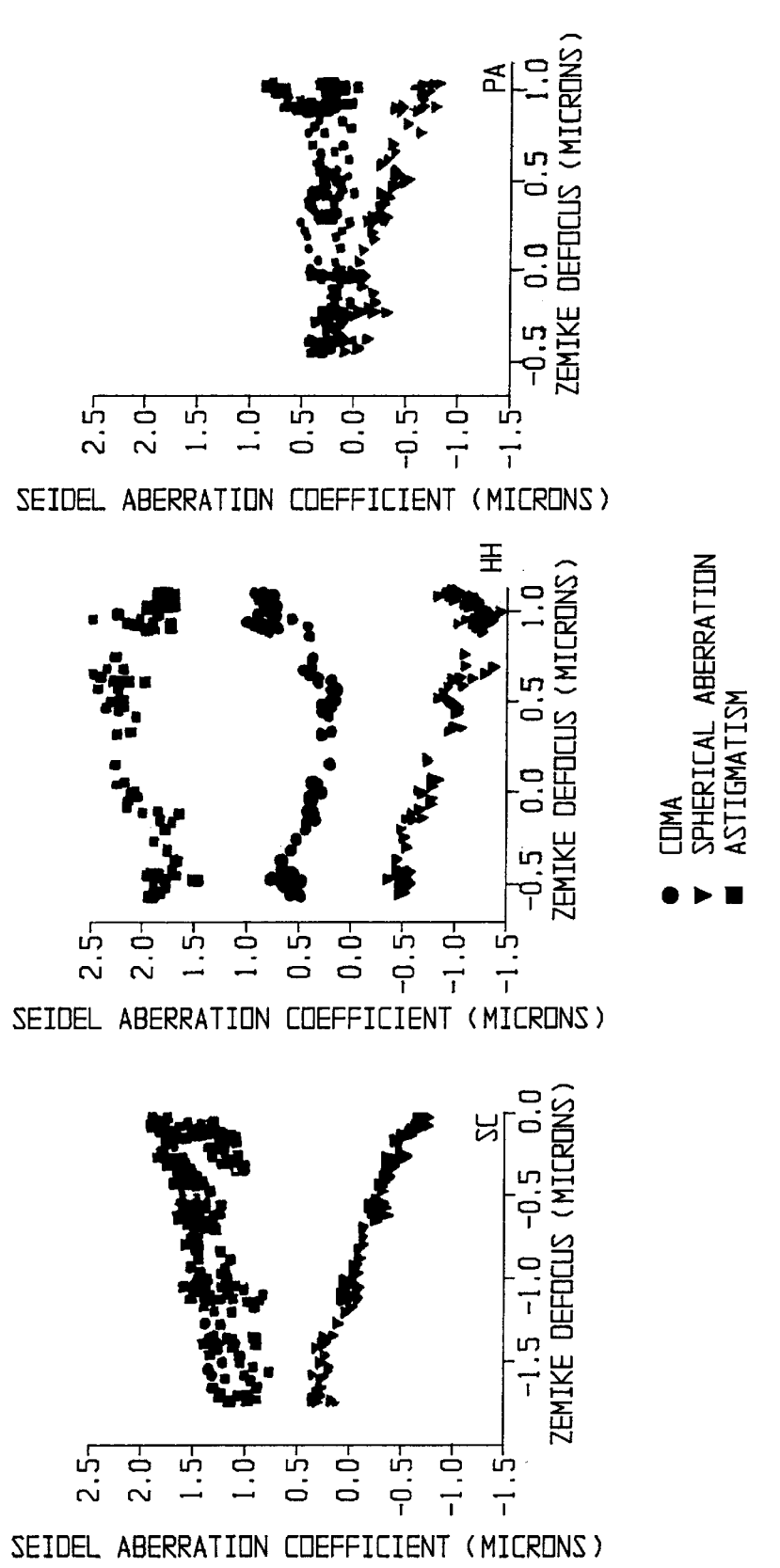
FIG. 4 shows plots, for three subjects, of measurements of the amount of coma, astigmatism, and spherical aberration when the subject changed his/her accommodation smoothly from one state to another.

FIG. 4 shows, for three subjects, SC, HH, and PA, a measurement of the amount of coma, astigmatism, and spherical aberration when the subject changed his/her accommodation smoothly from one state to another. Pupil size was 4.7 mm. The accommodative state is expressed as Zernike defocus in microns, where 1 micron is equivalent to 1.26 diopters of defocus. These data show that there is considerable individual variability between subjects in exactly how the aberrations change. Nonetheless, it is clear in each subject that there are substantial, systematic changes in the aberrations that are dependent on accommodative state. The implication of this is that a static optical element or refined surgical procedure that was designed for one viewing distance would be less effective for other distances.

Figure 5:
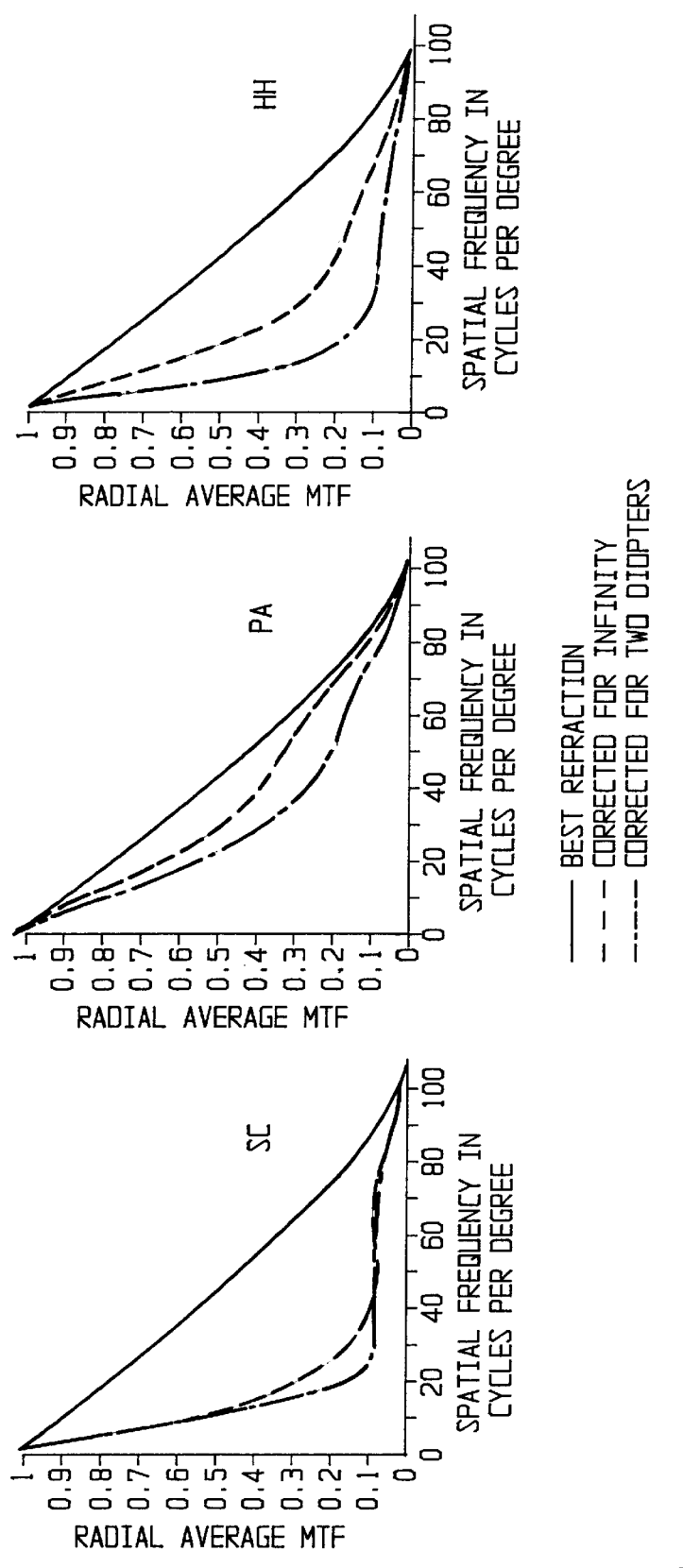
FIG. 5 illustrates modulation transfer functions computed from measurements of the three subjects' wave aberrations.

FIG. 5 illustrates this point with the modulation transfer functions (MTFs) computed from measurements of three subjects' wave aberrations. The Curve 1 for each subject shows the MTF that would be obtained if an ideal static correcting element were placed in front of the eye when it is focused at infinity. The pupil size for this calculation was 4.7 mm. This MTF shows the effects of diffraction alone. The Curve 2 shows the MTF when all the higher order aberrations (that is, those other than defocus) have been perfectly corrected had the subject been accommodating at infinity, when in fact the subject was accommodating at two diopters. It is important to keep in mind that defocus is not responsible for the fact that this curve lies way below the MTF when all aberrations are corrected, shown here. In fact, the amount of defocus has been optimized for this curve under the assumption that the subject's accommodation was perfect. For comparison purposes, also shown is the subject's MTF (Curve 3) when none of the higher order aberrations have been corrected for the same accommodative state. What this shows is that a static contact lens custom designed to correct perfectly all the higher order aberrations at one accommodative state does little or no good at correcting higher orders when the accommodative state is changed by two diopters. Though the changes of the wave aberration with accommodation limits the conditions under which a supercorrecting lens would provide a benefit in young people who can still accommodate, it does not imply that such a lens would have no use. This limitation is not particularly severe because it does not apply to presbyopes and, even in younger people, there would be value in designing the lens to correct for distance vision.

Rapid temporal fluctuations in the wave aberration might reduce the value of a static correction element. Though it has been known for some time that the eye's optics are not stable on short time scales, apart from the microfluctuations of accommodation, this instability has never been characterized. Short-term instability of the eye's aberrations will affect other types of wavefront correction besides a static element. For example, a previous wavefront sensor can be coupled to a deformable mirror (see the aforementioned U.S. Pat. No. 5,777,719, to correct most of the eye's aberrations, and can provide unprecedented retinal image quality, but its performance is fundamentally limited because the correction it applies is essentially static. Greater gains in optical performance could be achieved with a dynamic, real-time system capable of tracking the fluctuations in the eye's aberrations. Designing such a system requires knowledge of the wave aberration dynamics.

To measure these dynamics, in accordance with an embodiment of the invention, the real-time wavefront sensor 10 was used. The wavefront sensor 10 can also be coupled to a deformable mirror, like that in U.S. Pat. No. 5,777,719, to provide superb retinal image quality, as will be appreciated by those skilled in the art.

The bandwidth a perfect adaptive optics system would need to be able to keep up with these temporal fluctuations in the higher-order wave aberrations was investigated. How fast it would need to go so that to really achieve diffraction limited performance was addressed. To do this, the time averaged Strehl ratio, defined as the time averaged ratio of the peak height of the actual point spread function to the height of a diffraction limited point spread function that would be obtained after correction by a perfect adaptive optics system of various bandwidths was computed. The Strehl ratio is a metric often used to assess image quality. The curves for two subjects are shown in FIG. 18 for a 5.8 mm pupil and natural accommodation, one curve being the average. A Strehl ratio of 0.8 or above is considered to be diffraction limited. Also shown is the Strehl ratio for the best refracted case. Going from the best correction of defocus and astigmatism to the best static correction of all the monochromatic aberrations (which corresponds to zero bandwidth) goes almost all the way to diffraction limited performance. This is an important result because it implies that the error introduced by temporal dynamics of the eye's aberrations are small compared with the errors that can be corrected with a static correcting element. In other words, there is probably no need to worry very much that the dynamics of the wave aberration will obscure attempts to achieve better visual performance with a static-correcting element, such as a customized contact lens, or with refined surgical methods.

In order to go the rest of the way from perfect static correction to the diffraction limit, an adaptive optics (AO) system with a bandwidth of less than 1 Hz is needed. This does not mean that the eye does not exhibit fluctuations beyond a frequency of 1 Hz. It has been observed that significant frequency components exist at least out of 6 Hz or so. This simply means that for this pupil size and this condition the power carried by the fluctuations in frequencies above 1 Hz is just too small to significantly impact image quality, which is advantageous. A closed-loop AO correction requires a sampling rate at least 10–20 times the bandwidth of the fluctuations that are to be corrected, implying that an AO system operating at 10–20 Hz would be able to track all the significant fluctuations in the eye's optics for the 518 mm pupil size. This is encouraging because the technology to do this is available and the present invention achieves the first real-time AO correction for the eye In summary, the first measurements of the temporal properties of the eye's wave aberration have been demonstrated. These temporal fluctuations are small compared with the static higher order aberrations of the eye, implying that they will not interfere significantly with the benefits of a static customized optical element.

While a preferred embodiment and variations thereon have been set forth in detail above, those skilled in the art will appreciate that other embodiments can be realized within the scope of the invention. For example, while the hardware has been disclosed in terms of an Intel-based PC, another type of computer could be used, as could a dedicated device. Also, the software can be prepared according to any suitable programming techniques, such as object-oriented programming. Therefore, the invention should be construed as limited only by the appended claims.

What is claimed is:

1. A method of measuring a wavefront aberration of an eye, the method comprising:

(a) taking image data from the eye, the image data comprising a plurality of spots having positions determined by the wavefront aberration;

(b) defining a plurality of search boxes in the image data;
(c) determining the positions of the spots by
  (i) locating a centroid in each of the search boxes;
  (ii) replacing each of the search boxes with a search box of reduced size;
  (iii) locating the centroid in each of the search boxes of reduced size; and
  (iv) repeating steps (ii) and (iii) until each of the search boxes of reduced size reaches a minimum size; and
(d) calculating the wavefront aberration in accordance with the positions of the spots.

2. The method of claim 1, wherein:
step (a) is performed with a Hartmann-Shack detector having a plurality of lenslets; and
the plurality of lenslets form the plurality of spots.

3. The method of claim 2, wherein:
step (d) is performed using a matrix having rows corresponding to the lenslets; and
step (d) comprises:
  (i) determining which lenslets do not provide usable data; and
  (ii) eliminating the rows corresponding to the lenslets which do not provide usable data.

4. The method of claim 3, wherein step (d)(i) comprises allowing an operator to select the lenslets which do not provide usable data.

5. The method of claim 3, wherein step (d)(i) comprises determining automatically which lenslets do not provide usable data.

6. The method of claim 5, wherein step (d)(i) comprises determining automatically which lenslets do not provide usable data in accordance with standard deviations of intensity around the corresponding centroids.

7. The method of claim 5, wherein step (d)(i) comprises determining automatically which lenslets do not provide usable data in accordance with overall intensity levels of the corresponding centroids.

8. The method of claim 3, wherein:
the matrix has two rows corresponding to each of the lenslets; and
step (d)(ii) comprises eliminating both of the rows corresponding to each of the lenslets which do not provide usable data.

9. The method of claim 8, wherein the two rows corresponding to each of the lenslets are a row corresponding to an x coordinate and a row corresponding to ay coordinate.

10. The method of claim 3, wherein step (d) is performed using singular value decomposition.

11. The method of claim 1, wherein the minimum size is a diffraction limited size.

12. The method of claim 1, wherein step (c)(ii) comprises reducing a size of each search box to be replaced by one pixel in each direction.

13. The method of claim 1, wherein steps (c)(i) and (c)(iii) are performed only in accordance with pixels in the image data whose intensities lie between a lower threshold and an upper threshold.

14. The method of claim 6, further comprising prompting an operator to select the lower threshold and the upper threshold.

15. The method of claim 1, wherein each of the plurality of search boxes defined in step (b) is centered on a position which one of the spots would occupy in an absence of the wavefront aberration.

16. The method of claim 15, wherein each of the plurality of search boxes defined in step (b) has a dimension equal to a spacing between the positions which the spots would occupy in the absence of the wavefront aberration.

17. The method of claim 15, wherein each of the plurality of search boxes defined in step (b) has a dimension which is scaled down from a spacing between the positions which the spots would occupy in the absence of the wavefront aberration by a factor less than one.

18. The method of claim 17, wherein step (b) comprises prompting an operator for the factor.

19. The method of claim 1, wherein step (c)(ii) comprises reducing a size of each search box to be replaced by a fraction of a pixel along each side.

20. The method of claim 19, wherein the fraction of a pixel is one-half of a pixel.

21. The method of claim 19, wherein, for each search box of reduced size which includes at least one fractional pixel, step (c)(iii) comprises assigning to each of said at least one fractional pixel a contribution to the centroid which is equal to a corresponding fraction of an intensity detected in the fractional pixel centered in the fractional pixel.

22. The method of claim 1, wherein step (c) further comprises:
  (v) allowing an operator to drag one of the centroids to a new location; and
  (vi) recalculating the centroid which has been dragged to the new location, using a light distribution around the new location.

23. The method of claim 1, wherein step (c) further comprises:
  (v) allowing an operator to drag a central one of the centroids to a new location; and
  (vi) recalculating all of the centroids around the new location.

24. The method of claim 1, wherein step (c)(iii) is performed without reference to a location of a previously located centroid.

25. The method of claim 1, wherein step (c)(iii) is performed using a location of a previously located centroid as a start estimate.

26. The method of claim 1, wherein step (c)(iii) is performed using, as a start estimate, a location which a spot would occupy in an absence of the wavefront aberration.

27. The method of claim 1, wherein step (d) comprises calculating a number of Zernike modes by using a number of centroids which is at least twice the number of Zernike modes.

28. The method of claim 1, wherein step (d) comprises calculating the wavefront aberration for a first pupil radius $R_0$ of the eye and also for a second pupil radius $R_1$ of the eye, wherein $R_1 < R_0$.

29. The method of claim 28, wherein the wavefront aberration is calculated for $R_1$ by renormalizing the wavefront aberration calculated for $R_0$.

30. The method of claim 28, wherein step (d) further comprises prompting an operator for $R_1$.

31. The method of claim 30, wherein step (d) further comprises prompting an operator for a minimum Zernike mode and a maximum Zernike mode for use in calculating the wavefront aberration for $R_1$.

32. A system for measuring a wavefront aberration of an eye, the system comprising:
image data taking means for taking image data from the eye, the image data comprising a plurality of spots having positions determined by the wavefront aberration; and
computation means, receiving the image data, for:

(a) defining a plurality of search boxes in the image data;
(b) determining the positions of the spots by
   (i) locating a centroid in each of the search boxes;
   (ii) replacing each of the search boxes with a search box of reduced size;
   (iii) locating the centroid in each of the search boxes of reduced size; and
   (iv) repeating steps (ii) and (iii) until each of the search boxes of reduced size reaches a minimum size; and
(c) calculating the wavefront aberration in accordance with the positions of the spots.

33. The system of claim 32, wherein:
the image data taking means comprises a Hartmann-Shack detector having a plurality of lenslets; and
the plurality of lenslets form the plurality of spots.

34. The system of claim 33, wherein:
the computation means performs step (c) using a matrix having rows corresponding to the lenslets; and
step (c) comprises:
   (i) determining which lenslets do not provide usable data; and
   (ii) eliminating the rows corresponding to the lenslets which do not provide usable data.

35. The system of claim 34, further comprising interface means for allowing an operator to select the lenslets which do not provide usable data.

36. The system of claim 34, wherein step (c)(i) comprises determining automatically which lenslets do not provide usable data.

37. The system of claim 36, wherein step (c)(i) comprises determining automatically which lenslets do not provide usable data in accordance with standard deviations of intensity around the corresponding centroids.

38. The system of claim 36, wherein step (c)(i) comprises determining automatically which lenslets do not provide usable data in accordance with overall intensity levels of the corresponding centroids.

39. The system of claim 34, wherein:
the matrix has two rows corresponding to each of the lenslets; and
step (c)(ii) comprises eliminating both of the rows corresponding to each of the lenslets which do not provide usable data.

40. The system of claim 39, wherein the two rows corresponding to each of the lenslets are a row corresponding to an x coordinate and a row corresponding to a y coordinate.

41. The system of claim 34, wherein step (d) is performed using singular value decomposition.

42. The system of claim 32, wherein the minimum size is a diffraction limited size.

43. The system of claim 32, wherein step (b)(ii) comprises reducing a size of each search box to be replaced by one pixel in each direction.

44. The system of claim 32, wherein steps (b)(i) and (b)(iii) are performed only in accordance with pixels in the image data whose intensities lie between a lower threshold and an upper threshold.

45. The system of claim 44, further comprising interface means for prompting an operator to select the lower threshold and the upper threshold.

46. The system of claim 32, wherein each of the plurality of search boxes defined in step (a) is centered on a position which one of the spots would occupy in an absence of the wavefront aberration.

47. The system of claim 46, wherein each of the plurality of search boxes defined in step (a) has a dimension equal to a spacing between the positions which the spots would occupy in the absence of the wavefront aberration.

48. The system of claim 46, wherein each of the plurality of search boxes defined in step (a) has a dimension which is scaled down from a spacing between the positions which the spots would occupy in the absence of the wavefront aberration by a factor less than one.

49. The system of claim 48, further comprising interface means for prompting an operator for the factor.

50. The system of claim 32, wherein step (b)(ii) comprises reducing a size of each search box to be replaced by a fraction of a pixel along each side.

51. The system of claim 50, wherein the fraction of a pixel is one-half of a pixel.

52. The system of claim 50, wherein, for each search box of reduced size which includes at least one fractional pixel, step (b)(iii) comprises assigning to each of said at least one fractional pixel a contribution to the centroid which is equal to a corresponding fraction of an intensity detected in the fractional pixel centered in the fractional pixel.

53. The system of claim 32, further comprising interface means for allowing an operator to drag one of the centroids to a new location, and wherein step (b) further comprises recalculating the centroid which has been dragged to the new location, using a light distribution around the new location.

54. The system of claim 32, further comprising interface means for allowing an operator to drag a central one of the centroids to a new location, and wherein step (b) further comprises recalculating all of the centroids around the new location.

55. The system of claim 32, wherein step (b)(iii) is performed without reference to a location of a previously located centroid.

56. The system of claim 32, wherein step (b)(iii) is performed using a location of a previously located centroid as a start estimate.

57. The system of claim 32, wherein step (b)(iii) is performed using, as a start estimate, a location which a spot would occupy in an absence of the wavefront aberration.

58. The system of claim 32, wherein step (c) comprises calculating a number of Zernike modes by using a number of centroids which is at least twice the number of Zernike modes.

59. The system of claim 32, wherein step (c) comprises calculating the wavefront aberration for a first pupil radius $R_0$ of the eye and also for a second pupil radius $R_1$ of the eye, wherein $R_1 < R_0$.

60. The system of claim 59, wherein the wavefront aberration is calculated for $R_1$ by renormalizing the wavefront aberration calculated for $R_0$.

61. The system of claim 59, further comprising interface means for prompting an operator for $R_1$.

62. The system of claim 61, further comprising interface means for prompting an operator for a minimum Zernike mode and a maximum Zernike mode for use in calculating the wavefront aberration for $R_1$.

* * * * *

UNITED STATES PATENT AND TRADEMARK OFFICE
CERTIFICATE OF CORRECTION

PATENT NO. : 6,199,986 B1
DATED : March 13, 2001
INVENTOR(S) : Williams et al.

It is certified that error appears in the above-identified patent and that said Letters Patent is hereby corrected as shown below:

Column 1,
Line 3, the following statement should be included;

This invention was made under a contract with the National Eye Institute of the United States Government under Grant No. 5 R01 EY004367-16. The Government has certain rights in this invention.

Signed and Sealed this

Eighteenth Day of June, 2002

Attest:

Attesting Officer

JAMES E. ROGAN
Director of the United States Patent and Trademark Office